US007323585B2

(12) United States Patent
Xiang et al.

(10) Patent No.: US 7,323,585 B2
(45) Date of Patent: Jan. 29, 2008

(54) LEVODOPA PRODRUGS, AND COMPOSITIONS AND USES THEREOF

(75) Inventors: Jia-Ning Xiang, Palo Alto, CA (US); Mark A. Gallop, Los Altos, CA (US); Cindy X. Zhou, Palo Alto, CA (US); Mark Nguyen, San Jose, CA (US); Xuedong Dai, San Jose, CA (US); Jianhua Li, Sunnyvale, CA (US); Kenneth C. Cundy, Redwood City, CA (US)

(73) Assignee: XenoPort, Inc., Santa Clara, CA (US)

( * ) Notice: Subject to any disclaimer, the term of this patent is extended or adjusted under 35 U.S.C. 154(b) by 169 days.

(21) Appl. No.: 11/145,280

(22) Filed: Jun. 3, 2005

(65) Prior Publication Data

US 2006/0020028 A1    Jan. 26, 2006

Related U.S. Application Data

(60) Provisional application No. 60/577,065, filed on Jun. 4, 2004.

(51) Int. Cl.
*C07C 229/00* (2006.01)
*A01N 37/00* (2006.01)

(52) U.S. Cl. .......................................... 560/42; 514/529
(58) Field of Classification Search ...................... None
See application file for complete search history.

(56) References Cited

U.S. PATENT DOCUMENTS

| | | | |
|---|---|---|---|
| 3,811,444 A | 5/1974 | Heller et al. | |
| 3,962,414 A | 6/1976 | Michaels | |
| 3,992,518 A | 11/1976 | Chien et al. | |
| 4,066,747 A | 1/1978 | Capozza | |
| 4,070,347 A | 1/1978 | Schmitt | |
| 4,079,038 A | 3/1978 | Choi et al. | |
| 4,083,949 A | 4/1978 | Benedikt | |
| 4,093,709 A | 6/1978 | Choi et al. | |
| 4,134,991 A | 1/1979 | Wermuth | |
| 4,311,706 A | 1/1982 | Bodor et al. | |
| 4,663,349 A | 5/1987 | Repta | |
| 4,771,073 A | 9/1988 | Repta | |
| 4,826,875 A | 5/1989 | Chiesi | |
| 4,873,263 A | 10/1989 | Repta | |
| 4,966,915 A | 10/1990 | Tsuchiya et al. | |
| 4,983,400 A * | 1/1991 | Dempski et al. ............ | 514/565 |
| 5,017,607 A | 5/1991 | Chiesi | |
| 5,462,933 A | 10/1995 | Kramer et al. | |
| 5,607,969 A | 3/1997 | Milman et al. | |
| 5,827,819 A | 10/1998 | Yatvin et al. | |
| 5,840,756 A | 11/1998 | Cohen et al. | |
| 6,696,600 B2 * | 2/2004 | Frenkel et al. ............... | 562/445 |
| 2002/0099041 A1 | 7/2002 | Gallop et al. | |
| 2003/0158254 A1 | 8/2003 | Zerangue et al. | |

FOREIGN PATENT DOCUMENTS

| | | |
|---|---|---|
| EP | 0 309 827 B1 | 1/1992 |
| JP | 58-024547 | 2/1983 |
| WO | WO 86/04579 | 8/1986 |
| WO | WO 88/01615 | 3/1988 |
| WO | WO 02/28882 A1 | 4/2002 |

OTHER PUBLICATIONS

Marrel et al., "L-DOPA esters as potential prodrugs," *Eur. J. Med. Chem. Chim. Ther.*, 5:459-465 (1985).
International Search Report and Written Opinion mailed Nov. 3, 2005, for Application No. PCT/US2005/019493, filed Jun. 3, 2005.
International Search Report and Written Opinion mailed Nov. 3, 2005, for Application No. PCT/US2005/019492, filed Jun. 3, 2005.
Bai, 1995, "pGlu-L-Dopa-Pro: A Tripeptide Prodrug Targeting the Intestinal Peptide Transporter for Absorption and Tissue Enzymes for Conversion," *Pharmaceutical Research*, 12(7): 1101-1104.
Bodor et al., 1977, "Improved Delivery through Biological Membranes. 4. Prodrugs of L-Dopa," *Journal of Medicinal Chemistry*, 20(11): 1435-1445.
Coleman et al., 1990, "Polymer reviews: A practical guide to polymer miscibility," *Polymer*, 31: 1187-1203.
Cooper et al., 1987, "L-Dopa esters as potential prodrugs: behavioural activity in experimental models of Parkinson's disease," *J. Pharm. Pharmacol.*, 39: 627-635.
Di Stefano et al., 2001, "Dimeric L-Dopa Derivatives as Potential Prodrugs," *Bioorganic & Medicinal Chemistry Letters*, 11: 1085-1088.
During et al., 1989, "Controlled Release of Dopamine from a Polymeric Brain Implant: In Vivo Characterization," *Ann. Neurol.*, 25(4):351-356.
Felmeister, 1970, Chapter 86: Powders: Particle size reduction, classification, and measurement-mixing of powders-powders as a dosage form, pp. 1626-1628 from *Remington's Pharmaceutical Sciences, Fourteenth Edition*, Hoover (ed.), Mack Publishing Company, Easton, PA.
Fincher, 1968, "Particle Size of Drugs and Its Relationship to Absorption and Activity," *J. Pharm. Sci.*, 57(11): 1825-1835.
Fix et al., 1989, "Short-Chain Alkyl Esters of L-Dopa as Prodrugs for Rectal Absorption," *Pharmaceutical Research*, 6(6): 501-505.
Fix et al., 1990, "A Comparison of Oral and Rectal Absorption of L-Dopa Esters in Rats and Mice," *Pharm. Res.* 7(4):384-387.
Garzon-Aburbeh et al., 1986, "A Lymphotropic Prodrug of L-Dopa: Synthesis, Pharmacological Properties, and Pharmacokinetic Behavior of 1,3-Dihexadecanoyl-2-[(S)-2-amino-3-(3,4-dihydroxyphenyl)propanoyl]propane-1,2,3-triol," *J. Med. Chem.* 29: 687-691.
Gennaro (Ed.), 1985, Title Page and Table of Contents, in: *Remington's Pharmaceutical Sciences*, 17th Edition, Mack Publishing Co., Easton, PA.
Goodson, 1984, Chapter 6: Dental Applications, pp. 115-138 from *Medical Applications of Controlled Release, Volume II: Applications and Evaluation*, Langer and Wise (eds.), CRC Press, Inc., Boca Raton, FL.

(Continued)

*Primary Examiner*—Yvonne Eyler
*Assistant Examiner*—M Louisa Lao
(74) *Attorney, Agent, or Firm*—Finnegan, Henderson, Farabow, Garrett & Dunner, L.L.P.

(57) ABSTRACT

Prodrugs of levodopa, methods of making prodrugs of levodopa, methods of using prodrugs of levodopa, and compositions of prodrugs of levodopa are disclosed.

38 Claims, No Drawings

OTHER PUBLICATIONS

Greene and Wuts (eds.), 1991, Title page, Preface, and Contents from *Protective Groups in Organic Synthesis, Second Edition*, John Wiley & Sons, Inc., New York.

Greene and Wuts (eds.), 1999, Title page, Prefaces, and Contents from *Protective Groups in Organic Synthesis, Third Edition*, John Wiley & Sons, Inc., New York.

Harrison and Harrison (eds.), 1971-1995, Title pages, Prefaces, and Contents from *Compendium of Synthetic Organic Methods, vol. 1-8*, John Wiley & Sons, Inc. New York.

Hisaka et al., 1990, "Absorption of a Novel Prodrug of L-Dopa, L-3-(Hydroxy-4-Pivaloyloxphenyl)alanine (NB-355): In Vitro and In Situ Studies," *Drug Metabolism and Disposition*, 18(5): 621-625.

Hoes and Feijen, 1989, The Application of Drug-Polymer Conjugates in Chemotherapy, pp. 57-109 from *Horizons in Biochemistry and Biophysics vol. 9: Drug Carrier Systems*, John Wiley & Sons, New York.

Howard et al., 1989, "Intracerebral drug delivery in rats in lesion-induced memory deficits," *J. Neurosurg.*, 71: 105-112.

Ishikura et al., 1995, "Drug delivery to the brain. DOPA prodrugs based on a ring-closure reaction to quaternary thiazolium compounds," *Int'l Journal of Pharmaceutics*, 116: 51-63.

Juncos et al., 1987, "Levodopa methyl ester treatment of Parkinson's disease," *Neurology*, 37: 1242-1245.

King and Schwartz, 1985, Chapter 90: Oral Solid Dosage Forms, pp. 1603-1632 from *Pharmaceutical Sciences*, Mack Publishing Company, Easton, PA.

Langer, 1990, "New Methods of Drug Delivery," *Science*, 249: 1527-1533.

Langer and Peppas, 1983, "Chemical and Physical Structure of Polymers as Carriers for Controlled Release of Bioactive Agents: A Review," JMS-Rev. Macromol. Chem. Phys., C23(1):61-126.

Langer and Wise (eds.), 1984, Title page and Table of Contents from *Medical Applications of Controlled Release, vol. I: Classes of Systems and vol. II: Applications and Evaluation*, CRC Press, Inc., Boca Raton, FL.

Larock, 1999, Title Page and Contents from *Comprehensive Organic Transformations: A Guide to Functional Groups, Second Edition*, Wiley-VCH, New York.

Leong and Langer, 1987, "Polymeric controlled drug delivery," *Advanced Drug Delivery Reviews*, 1: 199-233.

Leppert et al., 1988, "The Effects of Carbidopa Dose and Time and Route of Adminstration of Systemic L-Dopa Levels in Rats," *Pharmaceutical Research*, 5(9): 587-591.

Levy et al., 1985, "Inhibition of Calcification of Bioprosthetic Heart Valves by Local Controlled-Release Diphosphonate," *Science*, 228: 190-192.

Linhardt, 1989, Chapter 2: Biodegradable Polymers for *Controlled Release of Drugs, pp. 53-95 from Controlled Release of Drugs: Polymers and Aggregate Systems*, M. Rosoff (ed.), VCH Publishers.

Lu and Yu, 1994, "Dimensionless presentation for drug release from a coated pure drug bead: 2. Experiment," *International Journal of Pharmaceutics*, 112: 117-124.

Mar. 1992, Title page and Contents from *Advanced Organic Chemistry: Reactions, Mechanisms, and Structure, Fourth Edition*, John Wiley & Sons, New York.

Roff et al. (eds.), 1971, Title Page, Preface, Acknowledgements, Contents, How to Use This Book, 1. List of Sections on Individual Polymers, and 2. List of Sections on Specific Properties and Related Information from *Handbook of Common Polymers: Fibres, Films, Plastics and Rubbers*, CRC Press, Cleveland, OH.

Sasahara et al., 1980, "Dosage Form Design for Improvement of Bioavailability of Levodopa II: Bioavailability of Marketed Levodopa Preparations in Dogs and Parkinsonian Patients," *Journal of Pharmaceutical Sciences*, 69(3): 261-265.

Saudek et al., 1989, "A Preliminary Trial of the Programmable Impantable Medication System for Insulin Delivery," *N. Engl. J. Med.*, 321:574-579.

Sefton, 1987, "Implantable Pumps," *CRC Critical Reviews in Biomedical Engineering*, 14(3):201-240.

Smith, 1994, Title Page and Contents from *Organic Synthesis*, McGraw-Hill, Inc., New York.

Smolen and Ball (eds.), 1984, Title Page and Contents from *Controlled Drug Bioavailability, vol. 1: Drug Product Design and Performance*, John Wiley & Sons, New York.

Verma et al., 2000, "Osmotically Controlled Oral Drug Delivery," *Drug Development and Industrial Pharmacy*, 26(7): 695-708.

Wang et al., 2002, "Preparation and Intestinal Absorption of L-Dopa-D-phenylglycine," *Journal of Food and Drug Analysis*, 10(2): 81-87.

Wang et al., 1995, "Synthesis and Pharmacological Activities of a Novel Tripeptide Mimetic Dopamine Prodrug," *Bioorganic & Medicinal Chemistry Letters*, 5(19): 2195-2198.

Xiang et al., "Levodopa Prodrugs, and Compositions and Uses Thereof," U.S. Appl. No. 11/145,159, filed Jun. 3, 2005.

\* cited by examiner

LEVODOPA PRODRUGS, AND COMPOSITIONS AND USES THEREOF

This application claims benefit to U.S. Provisional Application No. 60/577,065 filed Jun. 4, 2004, which is incorporated by reference herein in its entirety.

Embodiments of the present invention are directed to prodrugs of levodopa, methods of making prodrugs of levodopa, methods of using prodrugs of levodopa, and compositions of prodrugs of levodopa.

Parkinson's disease is a disabling, progressive illness that affects one in 1,000 people and generally occurs in people over the age of 50 years. Patients with Parkinson's disease have a deficiency of the neurotransmitter dopamine in the brain as a result of the nigrostriatal pathway disruption caused by degeneration of the substantia nigra. Levodopa (L-dopa or L-3,4-dihydroxyphenylalanine), an immediate precursor of dopamine, is the most commonly prescribed drug for treatment of this disease.

Following oral administration, levodopa is rapidly absorbed via an amino acid transporter present in the upper small intestine. Due to the narrow distribution of this transporter system, the window available for levodopa absorption is limited and the extent of absorption can be dependent on the rate at which the drug passes through the upper gastrointestinal tract. Approximately 35% of the administered dose reaches the systemic circulation as intact levodopa after oral administration in patients (Sasahara, 1980, *J. Pharm. Sci.*, 69, 261). The absolute bioavailability of levodopa is dose-dependent, due to saturation of the active transport pathway. Plasma levels of levodopa must be carefully titrated for each patient to achieve the optimal therapeutic activity. If the concentration of levodopa is too low in plasma (and consequently in the brain) the patient can experience a return of the symptoms of Parkinson's disease (rigidity, tremor, bradykinesia). On the other hand, motor fluctuation can become a significant side effect if plasma drug levels are too high. Uncontrolled fluctuations in plasma levodopa levels can greatly contribute to the incidence of "on-off" fluctuations (dyskinesias). The most effective control of Parkinsonism is observed when plasma levels of levodopa are maintained in a narrow range, for example, by continuous intraduodenal infusion.

Once absorbed, levodopa is rapidly converted to dopamine by L-aromatic amino acid decarboxylase (AADC) in the peripheral tissues (e.g., intestines and liver). It has been known that intestinal metabolism of levodopa is the major source of first pass loss of the drug. In patients, only 1% of the administered dose reaches the central nervous system intact, following transport across the blood-brain barrier by the neutral amino acid transporter. For this reason, levodopa is normally co-administered with a drug designed to inhibit its peripheral decarboxylation such as carbidopa or benserazide. When administered with carbidopa, the plasma intact levodopa amount increases and thus more levodopa becomes available to be transported into the central nervous system where it is converted to dopamine. Carbidopa itself does not cross the blood-brain barrier to a significant extent, and therefore does not inhibit the required conversion of levodopa to dopamine in the brain.

The oral bioavailability of levodopa from conventional formulations of levodopa/carbidopa (e.g., Sinemet®) is 84% to 99% (Physician's Desk Reference). The half-life of levodopa in the plasma of patients is about 50 min when administered alone, or 1 to 2 hrs when given with carbidopa. For this reason, the drug must be administered three or more times per day.

A formulation of levodopa/carbidopa (Sinemet® CR) intended to provide a controlled release of both drugs is commercially available. Sinemet® CR is designed for release of both levodopa and carbidopa over a 4 to 6 hour period. However, absorption of levodopa is limited to the small intestine and the resulting bioavailability of levodopa from Sinemet® CR is reduced relative to the immediate release product. In most cases, Sinemet® CR must also be given more than twice per day to achieve a therapeutic level of levodopa. Delayed and extended release formulations that release drug over periods of about 10 to 24 hours, and hence release much of the drug loading in the large intestine, have not been effective for delivering levodopa since levodopa is poorly absorbed from the large intestine. A simple enteric-coated formulation of levodopa led to increased gastrointestinal side effects (nausea) but did not improve absorption. A sustained release formulation of levodopa/carbidopa has been described that employs a swellable matrix (Geomatrix) delivery system to retain the drug in the stomach (Genta Jago product licensing information, June 1997). However, this formulation was designed to be bioequivalent to the commercially available Sinemet® CR formulation and therefore has not proven capable of providing the desired goal of a once or twice per day regimen.

The use of simple ester prodrugs of levodopa to improve the pharmacokinetics of the drug has been proposed (U.S. Pat. Nos. 5,017,607; 4,826,875; 4,873,263; 4,771,073; 4,663,349; 4,311,706; Japanese Patent No. JP58024547; Juncos et al., 1987, *Neurology*, 37:1242; and Cooper et al., 1987, *J. Pharm. Pharmacol.*, 39:627-635). An oral formulation of levodopa methyl ester (Levomet®, CHF 1301) has been described (Chiesi Pharmaceuticals). The ethyl ester of levodopa (TV-1203) is under clinical investigation as a potential therapy for Parkinsonism when co-administered with carbidopa (U.S. Pat. No. 5,607,969). A sustained cellulose formulation of levodopa ethyl ester in a mixture of hydroxypropylmethyl cellulose, hydroxypropyl cellulose, and a carboxyvinyl polymer has been described (U.S. Pat. No. 5,840,756). However, oral administration of this formulation to healthy adults pretreated with carbidopa produced a plasma levodopa terminal half-life of only 2 hr, comparable to that of Sinemet® CR.

A pivaloyl ester of levodopa (NB-355) has been described (European Patent No. 0 309 827). Following oral administration of NB-355, no rapid increase or elimination of levodopa was observed and duration time was prolonged, while levels of levodopa were low. The potential for using ester prodrugs of levodopa to enhance rectal absorption of the drug has been described (U.S. Pat. Nos. 4,663,349; 4,771,073; 4,873,263). Notably, the absorption of simple alkyl esters of levodopa has been shown to be greater following rectal absorption than following oral dosing (Fix, et al., *Pharm. Res.*, 1989, 6:501-5; Fix, et al., *Pharm. Res.*, 1990, 4:384-7). This effect is attributed to the decreased abundance of esterases in the large intestine relative to the small intestine. Therefore, selective delivery of a prodrug of levodopa to the large intestine in a sustained release formulation might be expected to provide a greater oral bioavailability and a prolonged exposure to the drug.

A series of glycolic acid ester containing prodrugs of levodopa has been described (Wermuth, U.S. Pat. No. 4,134, 991). Lipid conjugates of levodopa to facilitate the entry of drug into cells and tissues have also been described (Yatvin, U.S. Pat. No. 5,827,819).

The half-life of levodopa is prolonged and its bioavailability increased by the co-administration of carbidopa. Both drugs have relatively short half-lives of less than about 2 hours. Any method of sustained delivery of levodopa to the systemic circulation would therefore require a sufficient level of carbidopa to continuously inhibit peripheral decarboxylation of levodopa. In order to avoid the need for frequent (more than twice per day) dosing of levodopa and carbidopa, it is desirable to deliver both levodopa and carbidopa (or prodrug thereof) in a sustained manner. It has been proposed that rectal co-administration of an AADC inhibitor such as carbidopa with an ester prodrug of levodopa would be possible as a means to decrease metabolic clearance of levodopa (U.S. Pat. Nos. 4,663,349; 4,771,073; 4,873,263). However, studies in rats have since indicated that absorption of carbidopa following rectal administration is poor (Leppert et al., 1988, *Pharm. Res.*, 5:587-591).

Thus, the development of levodopa prodrugs that can be efficiently absorbed throughout the gastrointestinal tract, including the colon, and reduce first-pass metabolism of levodopa, is highly desirable.

Certain embodiments of the present invention are related to prodrugs of levodopa and derivatives of levodopa prodrugs, which are capable of undergoing absorption across the intestinal epithelium via active and/or passive transport.

Certain embodiments of the present invention are related to prodrugs of levodopa which are capable of undergoing absorption across the intestinal epithelium via active transport mechanisms, and more particularly to levodopa prodrugs that are substrates for organic cation transporters expressed throughout the gastrointestinal tract.

The human gastrointestinal tract includes the small intestine and the large intestine. The human small intestine is a convoluted tube about twenty feet in length between the stomach and large intestine. The small intestine is subdivided into the duodenum, the jejunum, and the ileum. The large intestine is about 5 feet in length and runs from the ileum to the anus. The large intestine is divided into the caecum, colon, and the rectum. The colon is divided into four parts including the ascending, traverse, descending, and the sigmoid flexure. In general, an orally ingested compound resides about 1 to 6 hours in the stomach, about 2 to 7 hours in the small intestine, and about 8 to 18 hours in the colon. Thus, the greatest period of time for sustained release of a compound occurs when the compound is passing through the colon.

Certain active transporter proteins are known to be expressed throughout the gastrointestinal tract. An active transporter refers to a membrane-bound protein that recognizes a substrate and affects the entry of the substrate into, or exit from a cell by carrier-mediated transport or receptor-mediated transport. Active transport includes movement of molecules across cellular membranes that is directly or indirectly dependent on an energy mediated process, such as for example is driven by ATP hydrolysis or an ion gradient, that occurs by facilitated diffusion mediated by interaction with specific transporter proteins, and that occurs through a modulated solute channel. For example, organic cation transporters such as OCTN1 and OCTN2 are expressed in the epithelial cells lining a human colon as well as in the small intestine.

Thus, levodopa prodrugs that act as substrates for one or more organic cation transporter can exhibit increased active transporter-mediated absorption during the extended period of time that the compound passes through the gastrointestinal tract. Increased absorption and in particular colonic absorption of levodopa prodrug can result in the increased systemic bioavailability of the compound over an extended period of time. Systemic bioavailability refers to the rate and extent of systemic exposure to a drug or an active metabolite thereof as reflected in the integrated systemic blood concentration over a period of time, also referred to as "area under the curve."

In certain embodiments, levodopa prodrugs are capable of absorption over a significant length of the gastrointestinal tract, including the large intestine, and in particular the colon. Such prodrugs can be incorporated into conventional sustained release formulations including osmotic delivery devices to provide sustained systemic exposure to levodopa upon oral administration to a patient. Many of such prodrugs can be coadministered with a decarboxylase inhibitor such as carbidopa or benserazide, or a prodrug thereof, and in some embodiments also formulated as sustained release compositions, with the carbidopa/levodopa prodrug compositions or benserazide/levodopa prodrug compositions together providing prolonged exposure to levodopa at levels necessary to affect sustained anti-Parkinson's therapy. Certain embodiments include carbidopa prodrugs that can block first-pass levodopa decarboxylation within the intestinal enterocytes either as the intact carbidopa prodrug, or through generation of carbidopa from carbidopa prodrug cleavage within the enterocytes and which can be cleaved to provide carbidopa in the systemic circulation. Decarboxylase inhibitor/levodopa prodrug or decarboxylase inhibitor prodrug/levodopa prodrug sustained release compositions can also be administered together with inhibitors of catechol O-methyltransferase (COMT) such as entacapone or tolcapone, to further block peripheral clearance of levodopa.

Among levodopa prodrugs contemplated by certain embodiments are prodrugs in which the carboxyl moiety of levodopa is masked to form a carboxyl ester, which can be cleaved in vivo to release the parent drug, e.g., levodopa. Optionally, the catechol moieties of levodopa can additionally be masked with promoieties, these promoieties being cleaved either before or after cleavage of the carboxyl ester promoiety.

Suitable catechol protecting moieties in the aforementioned prodrugs can be elaborated by functionalizing one or more of the phenolic hydroxy groups via acylation or other appropriate methods. The corresponding esters, carbonates, and (hemi)acetals/(hemi)ketals can be cleaved in vivo to regenerate the catechol moieties of the parent drug.

Certain embodiments of the present invention provide at least one levodopa prodrug of Formula (I)

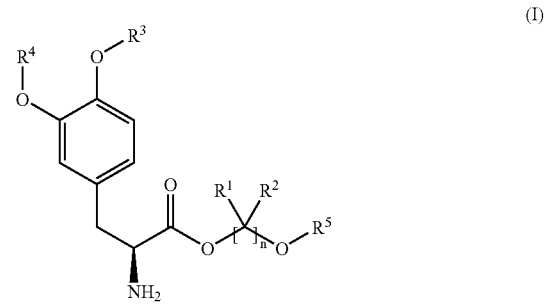

a stereoisomer thereof, an enantiomer thereof, a pharmaceutically acceptable salt thereof, a hydrate thereof, or a solvate of any of the foregoing, wherein n is an integer from 1 to 6;

each $R^1$ and $R^2$ is independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, halo, heteroalkyl, substituted heteroalkyl, heteroaryl, substituted heteroaryl, heteroarylalkyl, and substituted heteroarylalkyl, or optionally, when n is 1, then $R^1$ and $R^2$ together with the carbon atom to which $R^1$ and $R^2$ are attached form a cycloalkyl, substituted cycloalkyl, cycloheteroalkyl or substituted cycloheteroalkyl ring;

$R^3$ and $R^4$ are independently selected from hydrogen, —C(O)O$R^7$, —C(O)$R^7$, and —(C$R^8R^9$)OC(O)$R^{10}$;

$R^5$ is selected from alkyl, substituted alkyl, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl;

$R^7$ is selected from alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

$R^8$ and $R^9$ are independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, and substituted heteroarylalkyl or optionally, $R^8$ and $R^9$ together with the carbon atom to which $R^8$ and $R^9$ are attached form a cycloalkyl, substituted cycloalkyl, cycloheteroalkyl or substituted cycloheteroalkyl ring; and $R^{10}$ is selected from hydrogen, alkyl, substituted alkyl, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl;

with the provisos that when n is 2, and $R^1$, $R^2$, $R^3$ and $R^4$ are hydrogen, then $R^5$ is not hydrogen, methyl, or phenyl;

when n is 3, and $R^1$, $R^2$, $R^3$ and $R^4$ are hydrogen, then $R^5$ is not methyl; and when n is an integer from 1 to 6, and $R^1$, $R^2$, $R^3$ and $R^4$ are hydrogen, then $R^5$ is not benzyl.

Certain embodiments of the present invention provide compositions comprising at least one levodopa prodrug. In certain embodiments, the compositions comprise at least one levodopa prodrug, or an enantiomer and stereoisomer of any of the foregoing, or a pharmaceutically acceptable salt thereof, a hydrate thereof, or a solvate of any of the foregoing and a pharmaceutically acceptable diluent, carrier, excipient and/or adjuvant of any of the foregoing. The choice of diluent, carrier, excipient and/or adjuvant can depend upon, among other factors, the desired mode of administration.

Certain embodiments of the present invention provide methods of treating Parkinson's disease. The methods comprise co-administering to a patient in need of such treatment a therapeutically effective amount of at least one of following combinations: (i) at least one levodopa prodrug; (ii) at least one levodopa prodrug and decarboxylase inhibitor; (iii) at least one levodopa prodrug and at least one decarboxylase inhibitor prodrug; (iv) a stereoisomer or an enantiomer of any of the foregoing; and (v) a pharmaceutically acceptable salt thereof, a hydrate thereof or a solvate of any of the foregoing, are included in the embodiments. In certain embodiments, the at least one combination is administered to a patient using a sustained-release dosage form or device.

In certain embodiments, the at least one levodopa prodrug can be released from the dosage form, e.g., an orally administered dosage form, over a sufficient period of time to provide prolonged therapeutic concentrations of levodopa in the blood of a patient enabling administration of the dosage form on only a once or twice per day basis. In certain embodiments, the at least one levodopa prodrug can maintain a therapeutic or prophylactic blood concentration of levodopa or levodopa prodrug in the systemic circulation of a patient following oral administration of a levodopa prodrug over a period of at least 4 hours, in certain embodiments, over a period of at least 8 hours, and in certain embodiments, over a period of at least 12 hours. Similarly, a decarboxylase inhibitor (e.g., carbidopa, benserazide or prodrug thereof), when dosed with a levodopa prodrug, can be released from the dosage form or device immediately after the dosage form is administered, over a period of hours up to, for example, 16 hours after administration of the dosage form with greater than 75% of the decarboxylase inhibitor released, or coextensively released with the release of the levodopa prodrug.

The oral sustained release dosage forms or devices used with certain embodiments can take any form as long as the release characteristics and pharmacokinetic profiles above are satisfied. For example, the dosage form can be in the form of an osmotic dosage form, a prodrug-releasing polymer, prodrug-releasing tiny timed-release pills, prodrug-releasing lipids, prodrug-releasing waxes and/or prodrug-releasing beads.

Certain embodiments of the present invention provide compositions for treating Parkinson's disease in a patient in need of such treatment.

Certain embodiments of the present invention provide methods for making levodopa prodrugs, compositions comprising at least one levodopa prodrug, methods of using levodopa prodrugs, and methods of using compositions comprising at least one levodopa prodrug for treating Parkinson's disease.

SPECIFIC EMBODIMENTS

Definitions

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the embodiments are approximations, the numerical values set forth in the specific examples are reported as precisely as possible. Any numerical values, however, inherently contain certain errors necessarily resulting form the standard deviation found in their respective testing measurements.

To the extent the definitions of terms in the publications, patents, and patent applications incorporated herein by reference are not the same as the definitions set forth in this specification, the definitions in this specification control for the entire specification, including the claims. Any other definitions in the publications, patents, and patent applications incorporated herein by reference that are not explicitly provided in this specification apply only to the embodiments discussed in the publications, patents, and patent applications incorporated herein by reference.

"Compounds" refers to compounds encompassed by generic formulae disclosed herein, any subgenus of those generic formulae, and any specific compounds within those generic or subgeneric formulae. The compounds can be a specific specie, a subgenus or larger genus identified either by their chemical structure and/or chemical name. Further, compounds also include substitutions or modifications of any of such species, subgenuses or genuses, which are set forth herein. When the chemical structure and chemical name conflict, the chemical structure is determinative of the identity of the compound. The compounds can contain one or more chiral centers and/or double bonds and therefore, can exist as stereoisomers, such as double-bond isomers (i.e., geometric isomers), enantiomers or diastereomers. Accordingly, the chemical structures within the scope of the specification encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Further, when partial structures of the compounds are illustrated, asterisks indicate the point of attachment of the partial structure to the rest of the molecule. Enantiomeric and stereoisomeric mixtures can be resolved into their component enantiomers or stereoisomers using separation techniques or chiral synthesis techniques well known to the skilled artisan.

"Alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In certain embodiments, an alkyl group comprises from 1 to 20 carbon atoms.

"Alkanyl" refers to a saturated branched, straight-chain or cyclic alkyl group derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl; butanyls such as butan-1-yl, butan-2-yl (sec-butyl), 2-methyl-propan-1-yl (isobutyl), 2-methyl-propan-2-yl (t-butyl), cyclobutan-1-yl; and the like.

"Alkenyl" refers to an unsaturated branched, straight-chain or cyclic alkyl group having at least one carbon-carbon double bond derived by the removal of one hydrogen atom from a single carbon atom of a parent alkene. The group can be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, and the like.

"Alkylene" refers to an unsaturated branched, straight-chain or cyclic alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl, and the like.

"Alkylene" refers to a saturated or unsaturated, branched, straight-chain or cyclic divalent hydrocarbon group derived by the removal of two hydrogen atoms from a parent alkane, alkene or alkyne. Typical alkylene groups include, but are not limited to methylene, ethylene, propylene, butylene, and the like.

"Acyl" refers to a radical —C(O)R, where R is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cylcohexylcarbonyl, cyclohexylmethylcarbonyl, benzoyl, benzylcarbonyl and the like.

"Alkoxy" refers to a radical —OR where R represents an alkyl or cycloalkyl group as defined herein. Representative examples include, but are not limited to, methoxy, ethoxy, propoxy, butoxy, cyclohexyloxy, and the like.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group comprises from 6 to 20 carbon atoms.

"Arylene" refers to a divalent aromatic hydrocarbon group derived by removal of two hydrogen atoms from a parent aromatic ring system.

"Arylalkyl" refers to an acyclic alkyl group in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, and/or arylalkynyl is used. In certain embodiments, an arylalkyl group is ($C_6$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$).

"Arylalkylene" refers to a divalent acyclic alkyl group in which one of the hydrogen atoms bonded to a carbon atom, typically a terminal or sp³ carbon atom is replaced with an aryl group.

"Arylalkyloxy" refers to an —O-arylalkyl group where arylalkyl is as defined herein.

"Cyano" refers to the radical —CN.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. In a certain embodiment, the cycloalkyl group is ($C_3$-$C_{10}$) cycloalkyl, or in certain embodiments ($C_3$-$C_6$) cycloalkyl.

"Cycloheteroalkyl" refers to a saturated or unsaturated cyclic alkyl group in which one or more carbon atoms (and any associated hydrogen atoms) are independently replaced with the same or different heteroatom. Typical heteroatoms to replace the carbon atom(s) include, but are not limited to, N, P, O, S, and Si. Where a specific level of saturation is intended, the nomenclature "cycloheteroalkanyl" or "cycloheteroalkenyl" is used. Typical cycloheteroalkyl groups include, but are not limited to, groups derived from epoxides, imidazolidine, morpholine, piperazine, piperidine, pyrazolidine, pyrrolidine, quinuclidine, and the like.

"Compound of Formula (I) derived from 1,3-dihexadecanoylpropane-1,2,3-triol" refers to a moiety of structural formula:

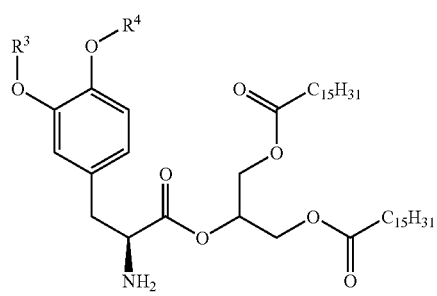

"Halo" refers to fluoro, chloro, bromo, or iodo.

"Heteroalkyloxy" refers to an —O-heteroalkyl group where heteroalkyl is as defined herein.

"Heteroalkyl, Heteroalkanyl, Heteroalkenyl Heteroalkynyl" refer to alkyl, alkanyl, alkenyl, and alkynyl groups, respectively, in which one or more of the carbon atoms (and any associated hydrogen atoms) are each independently replaced with the same or different heteroatomic groups. Typical heteroatomic groups include, but are not limited to, —O—, —S—, —O—O—, —S—S—, —O—S—, —NR'—, =N—N=, —N=N—, —N=N—NR'—, —PH—, —P(O)$_2$—, —O—P(O)$_2$—, —S(O)—, —S(O)$_2$—, —SnH$_2$—, and the like, wherein R' is hydrogen, alkyl, substituted alkyl, cycloalkyl, substituted cycloalkyl, aryl or substituted aryl.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group is between 5-20 membered heteroaryl, and in other embodiments is between 5-10 membered heteroaryl. In certain embodiments, heteroaryl groups are those derived from thiophene, pyrrole, benzothiophene, benzofuran, indole, pyridine, quinoline, imidazole, oxazole, and pyrazine.

"Heteroaryloxycarbonyl" refers to a radical —C(O)—OR where R is heteroaryl as defined herein.

"Heteroarylalkyl" refers to an acyclic alkyl group in which one of the hydrogen atoms bonded to a carbon atom, typically a terminal or sp³ carbon atom, is replaced with a heteroaryl group. Where specific alkyl moieties are intended, the nomenclature heteroarylalkanyl, heteroarylalkenyl, and/or heteroarylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl.

"Leaving group" has the meaning conventionally associated with it in synthetic organic chemistry, i.e., an atom or a group capable of being displaced by a nucleophile and includes halo (such as chloro, bromo, and iodo), acyloxy (e.g., acetoxy, and benzoyloxy), mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable" refers to approved or approvable by a regulatory agency of the Federal or a state government or listed in the U.S. Pharmacopeia or other generally recognized pharmacopeia for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable vehicle" refers to a diluent, adjuvant, excipient or carrier with which a compound is administered.

"Extended release" refers to dosage forms that provide for the delayed, slowed, over a period of time, continuous, discontinuous, or sustained release of the compounds.

"Patient" includes mammals and humans. The terms "human" and "patient" are used interchangeably herein.

"Prodrug" refers to a derivative of a drug molecule that requires a transformation within the body to cause the active drug to be formed. Prodrugs are frequently (though not necessarily) pharmacologically inactive until converted to the parent drug.

"Promoiety" refers to a group that is covalently attached to an active molecule that is potentially cleavable in vivo by enzymatic or non-enzymatic means. A promoiety can be, for example, a protecting group used to mask a functional group, a group that acts as a substrate for one or more active or passive transport mechanisms, or a group that acts to impart or enhance a certain property to the molecule, such as, for example, solubility.

"Protecting group" refers to a grouping of atoms that when attached to a reactive group in a molecule masks, reduces or prevents that reactivity. Examples of protecting groups can be found in Green et al., "Protective Groups in Organic Chemistry," (Wiley, 2$^{nd}$ ed. 1991) and Harrison et al., "Compendium of Synthetic Organic Methods," Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC"), and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers, and allyl ethers.

"Substituted" refers to a group in which one or more hydrogen atoms are each independently replaced with the same or different substituent(s). Typical substituents include, but are not limited to, —X, —R$^{33}$, —O$^-$, =O, —OR$^{33}$, —SR$^{33}$, —S$^-$, =S, —NR$^{33}$R$^{34}$, =NR$^{33}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{33}$, —OS(O$_2$)O$^-$, —OS(O)$_2$R$^{33}$, —P(O)(O$^-$)$_2$, —P(O)()R$^{33}$)(O$^-$), —OP(O)(OR$^{33}$)(OR$^{34}$), —C(O)R$^{33}$, —C(S)R$^{33}$, —C(O)OR$^{33}$, C(O)NR$^{33}$R$^{34}$, —C(O)O$^-$, —C(S)OR$^{33}$ NR$^{35}$C(O)NR$^{33}$R$^{34}$, —NR$^{35}$C(S)NR$^{33}$R$^{34}$, —NR$^{35}$C(NR$^{33}$)NR$^{33}$R$^{34}$, and —C(NR$^{33}$)NR$^{33}$R$^{34}$, where each X is independently a halogen; each R$^{33}$ and R$^{34}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{35}$R$^{36}$, —C(O)R$^{35}$ or —S(O)$_2$R$^{35}$ or optionally R$^{33}$ and R$^{34}$ together with the atom to which R$^{33}$ and R$^{34}$ are attached form a cycloheteroalkyl or substituted cycloheteroalkyl ring; and R$^{35}$ and R$^{36}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl. In certain embodiments, a substituent group is selected from halo, —CN, —NO$_2$, —OH, C$_{1-6}$ alkyl, and C$_{1-6}$ alkoxy. In certain embodiments, a substituent group is selected from halo, —OH, C$_{1-3}$ alkyl, and C$_{1-3}$ alkoxy.

"Treating" or "treatment" of any disease or disorder refers to arresting or ameliorating a disease or disorder, reducing the risk of acquiring a disease or disorder, reducing the development of a disease or disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and inhibit at least one physical parameter which may not be discernible to the patient. Further, "treating" or "treatment" refers to delaying the onset of the disease or disorder or at least symptoms thereof in a patient which may be exposed to or predisposed to a disease or disorder even though that patient does not yet experience or display symptoms of the disease or disorder.

"Therapeutically effective amount" refers to the amount of a compound that, when administered to a patient for treating a disease or disorder, is sufficient to affect such treatment for the disease or disorder. The "therapeutically effective amount" will vary depending on the compound, the disease or disorder and its severity and the age and weight of the patient to be treated.

"Cleave" refers to breakage of chemical bonds and is not limited to chemical or enzymatic reactions or mechanisms unless clearly indicated by the context.

Reference will now be made in detail to certain embodiments.

Compounds

Compounds include levodopa prodrugs and other derivatives to which promoieties have been attached. In certain embodiments, compounds include levodopa prodrugs of Formula (I):

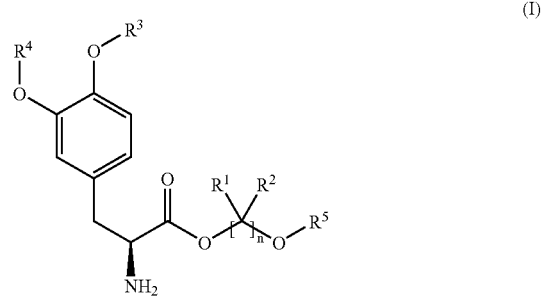

(I)

a stereoisomer thereof, an enantiomer thereof, a pharmaceutically acceptable salt thereof, a hydrate thereof, or a solvate of any of the foregoing, wherein n is an integer from 1 to 6;

each R$^1$ and R$^2$ is independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, halo, heteroalkyl, substituted heteroalkyl, heteroaryl, substituted heteroaryl, heteroarylalkyl, and substituted heteroarylalkyl, or optionally, when n is 1, then R$^1$ and R$^2$ together with the carbon atom to which R$^1$ and R$^2$ are attached form a cycloalkyl, substituted cycloalkyl, cycloheteroalkyl or substituted cycloheteroalkyl ring;

R$^3$ and R$^4$ are independently selected from hydrogen, —C(O)OR$^7$, —C(O)R$^7$, and —(CR$^8$R$^9$)OC(O)R$^{10}$;

$R^5$ is selected from alkyl, substituted alkyl, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl;

$R^7$ is selected from alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;

$R^8$ and $R^9$ are independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, and substituted heteroarylalkyl or optionally, $R^8$ and $R^9$ together with the carbon atom to which $R^8$ and $R^9$ are attached form a cycloalkyl, substituted cycloalkyl, cycloheteroalkyl or substituted cycloheteroalkyl ring; and $R^{10}$ is selected from hydrogen, alkyl, substituted alkyl, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl;

with the provisos that when n is 2, and $R^1$, $R^2$, $R^3$ and $R^4$ are hydrogen, then $R^5$ is not hydrogen, methyl or phenyl;

when n is 3, and $R^1$, $R^2$, $R^3$ and $R^4$ are hydrogen, then $R^5$ is not methyl; and when n is an integer from 1 to 6, and $R^1$, $R^2$, $R^3$ and $R^4$ are hydrogen, then $R^5$ is not benzyl.

In certain embodiments of a compound of Formula I, each $R^1$ and $R^2$ is independently selected from hydrogen, alkanyl, substituted alkanyl, arylalkanyl, substituted arylalkanyl, cycloalkanyl, substituted cycloalkanyl, cycloheteroalkanyl, substituted cycloheteroalkanyl, halo, heteroalkanyl, substituted heteroalkanyl, heteroarylalkanyl, and substituted heteroarylalkanyl.

In certain embodiments of a compound of Formula I, each $R^1$ and $R^2$ is independently selected from hydrogen, methyl, ethyl, propyl, isopropyl, butyl, isobutyl, sec-butyl, tert-butyl, cyclopropyl, cyclobutyl, cyclopentyl, cyclohexyl, and benzyl.

In certain embodiments of a compound of Formula I, each $R^1$ and $R^2$ is independently selected from hydrogen, aryl, substituted aryl, heteroaryl, and substituted heteroaryl.

In certain embodiments of a compound of Formula I, each $R^1$ and $R^2$ is independently selected from hydrogen and phenyl, which is optionally substituted with one or more substituents selected from halo, —CN, —NO$_2$, —OH, $C_{1-6}$ alkyl, and $C_{1-6}$ alkoxy.

In certain embodiments of a compound of Formula I, n is 1, and $R^1$ and $R^2$ together with the carbon atoms to which $R^1$ and $R^2$ are attached form a cycloalkanyl, substituted cycloalkanyl, cycloheteroalkanyl or substituted cycloheteroalkanyl ring.

In certain embodiments of a compound of Formula I, n is 1, and $R^1$ and $R^2$ together with the carbon atoms to which $R^1$ and $R^2$ are attached form a cyclopropyl, cyclobutyl, cyclopentyl or cyclohexyl ring.

In certain embodiments of a compound of Formula I, each $R^1$ and $R^2$ is independently selected from hydrogen, $C_{1-4}$ alkyl, and substituted $C_{1-4}$ alkyl.

In certain embodiments, each $R^1$ and $R^2$ is hydrogen.

In certain embodiments of a compound of Formula I, $R^5$ is selected from alkanyl, substituted alkanyl, alkenyl, substituted alkenyl, arylalkanyl, substituted arylalkanyl, arylalkenyl, substituted arylalkenyl, cycloalkanyl, substituted cycloalkanyl, cycloheteroalkanyl, substituted cycloheteroalkanyl, heteroarylalkanyl, and substituted heteroarylalkanyl. In certain embodiments of a compound of Formula I, $R^5$ is selected from methyl, ethyl, propyl, isopropyl, butyl, isobutyl, sec-butyl, tert-butyl, pentyl, hexyl, cyclopropyl, cyclobutyl, cyclopentyl, cyclohexyl, benzyl, phenethyl, and styryl, where the aryl ring of the benzyl or styryl group is optionally substituted with one or more substituents selected from halo, —CN, —NO$_2$, —OH, $C_{1-6}$ alkyl, and $C_{1-6}$ alkoxy.

In certain embodiments of a compound of Formula I, $R^5$ is selected from aryl, substituted aryl, heteroaryl, and substituted heteroaryl.

In certain embodiments of a compound of Formula I, $R^5$ is selected from $C_{5-8}$ aryl, and substituted $C_{5-8}$ aryl substituted with one or more substituents selected from halo, —CN, —NO$_2$, —OH, $C_{1-6}$ alkyl, and $C_{1-6}$ alkoxy.

In certain embodiments of a compound of Formula I, $R^5$ is selected from phenyl and pyridyl, which are optionally substituted with halo, —CN, —OH, $C_{1-4}$ alkyl, and $C_{1-4}$ alkoxy.

In certain embodiments of a compound of Formula I, $R^3$ and $R^4$ are independently selected from hydrogen, —C(O)OR$^7$, and —C(O)R$^7$. In certain embodiments, $R^7$ is selected from $C_{1-10}$ alkyl, substituted $C_{1-10}$ alkyl, $C_{5-8}$ aryl, $C_{5-8}$ substituted aryl, $C_{6-10}$ arylalkyl, and substituted $C_{6-10}$ arylalkyl.

In certain embodiments of a compound of Formula I, $R^7$ is selected from alkanyl, substituted alkanyl, cycloalkanyl, substituted cycloalkanyl, arylalkanyl, substituted arylalkanyl, heteroarylalkanyl, and substituted heteroarylalkanyl. In certain embodiments, $R^7$ is selected from methyl, ethyl, propyl, isopropyl, butyl, isobutyl, sec-butyl, tert-butyl, cyclopropyl, cyclobutyl, cyclopentyl, cyclohexyl, and benzyl, where the aryl ring of the benzyl group is optionally substituted with one or more substituents selected from halo, —CN, —NO$_2$, —OH, $C_{1-6}$ alkyl, and $C_{1-6}$ alkoxy.

In certain embodiments of a compound of Formula I, $R^7$ is selected from aryl, substituted aryl, heteroaryl, and substituted heteroaryl. In certain embodiments, $R^7$ is selected from phenyl, pyridyl, furyl, and thienyl, the aromatic rings of which are optionally substituted with one or more substituents selected from halo, —CN, —NO$_2$, —OH, $C_{1-6}$ alkyl, and $C_{1-6}$ alkoxy.

In certain embodiments of a compound of Formula I, $R^3$ and $R^4$ are independently selected from hydrogen, and —(CR$^8$R$^9$)OC(O)R$^{10}$.

In certain embodiments of a compound of Formula I, $R^8$ and $R^9$ are independently selected from hydrogen, $C_{1-16}$ alkyl, substituted $C_{1-6}$ alkyl, $C_{5-8}$ aryl, substituted $C_{5-8}$ aryl, $C_{6-10}$ arylalkyl, and substituted $C_{6-10}$ arylalkyl.

In certain embodiments of a compound of Formula I, $R^8$ and $R^9$ are independently selected from hydrogen, methyl, ethyl, propyl, isopropyl, butyl, and isobutyl.

In certain embodiments of a compound of Formula I, $R^{10}$ is selected from hydrogen, $C_{1-10}$ alkyl, substituted $C_{1-10}$ alkyl, $C_{5-8}$ aryl, substituted $C_{5-8}$ aryl, $C_{1-15}$ alkoxy, and substituted $C_{1-15}$ alkoxy.

In certain embodiments of a compound of Formula I, $R^{10}$ is selected from methyl, ethyl, propyl, isopropyl, butyl, isobutyl, sec-butyl, tert-butyl, cyclopropyl, cyclobutyl, cyclopentyl, cyclohexyl, benzyl, and phenyl, where the aryl ring of the benzyl group is optionally substituted with one or more substituents selected from halo, —CN, —NO$_2$, —OH, C$_{1-6}$ alkyl, and C$_{1-6}$ alkoxy.

In certain embodiments of a compound of Formula I, the compound is selected from:

2-(4-Fluorophenoxy)ethyl (2S)-2-amino-3-(3,4-dihydroxyphenyl)propanoate;
2-(4-Chlorophenoxy)ethyl (2S)-2-amino-3-(3,4-dihydroxyphenyl)propanoate;
2-(4-Methylphenoxy)ethyl (2S)-2-amino-3-(3,4-dihydroxyphenyl)propanoate;
2-(4-Methoxyphenoxy)ethyl (2S)-2-amino-3-(3,4-dihydroxyphenyl)propanoate;
2-(2-Fluorophenoxy)ethyl (2S)-2-amino-3-(3,4-dihydroxyphenyl)propanoate;
2-(4-Butylphenoxy)ethyl (2S)-2-amino-3-(3,4-dihydroxyphenyl)propanoate;
2-(3-Fluorophenoxy)ethyl (2S)-2-amino-3-(3,4-dihydroxyphenyl)propanoate;
2-(4-tert-Butylphenoxy)ethyl (2S)-2-amino-3-(3,4-dihydroxyphenyl)propanoate;
2-(4-Isopropylphenoxy)ethyl (2S)-2-amino-3-(3,4-dihydroxyphenyl)propanoate;
2-(4-Ethylphenoxy)ethyl (2S)-2-amino-3-(3,4-dihydroxyphenyl)propanoate;
2-(2,4-Dimethylphenoxy)ethyl (2S)-2-amino-3-(3,4-dihydroxyphenyl)propanoate;
2-(3,4-Dimethylphenoxy)ethyl (2S)-2-amino-3-(3,4-dihydroxyphenyl)propanoate;
2-(4-Fluorophenoxy)ethyl (2S)-2-amino-3-(3,4-diethoxycarbonyloxyphenyl)propanoate;
3-Phenoxypropyl (2S)-2-amino-3-(3,4-dihydroxyphenyl)propanoate;
3-(4-Fluorophenoxy)propyl (2S)-2-amino-3-(3,4-dihydroxyphenyl)propanoate;
(2R)-2-(4-Fluorophenoxy)isopropyl (2S)-2-amino-3-(3,4-dihydroxyphenyl)propanoate;
(2S)-2-(4-Fluorophenoxy)isopropyl (2S)-2-amino-3-(3,4-dihydroxyphenyl)propanoate; and
pharmaceutically acceptable salts thereof.

In certain embodiments of the above compounds, the pharmaceutically acceptable salt is the hydrochloride salt.

Synthesis of Certain Compounds

Embodiments of levodopa prodrugs can be prepared by methods well known in the art.

In certain embodiments the compounds can be prepared from readily available starting materials using the following general methods and procedures. It will be appreciated that where typical or preferred process conditions (i.e., reaction temperatures, times, mole ratios of reactants, solvents, pressures) are given, other process conditions can also be used unless otherwise stated. Optimum reaction conditions can vary with the particular reactants or solvent used, but such conditions can be determined by one skilled in the art by routine optimization procedures.

Additionally, as will be apparent to those skilled in the art, conventional protecting groups can be used to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis* and references cited therein.

Furthermore, in certain embodiments, the levodopa prodrugs can contain one or more chiral centers. Accordingly, such compounds can be prepared or isolated as pure stereoisomers, i.e., as individual enantiomers or diastereomers, or as stereoisomer-enriched mixtures. All such stereoisomers (and enriched mixtures) are included within the scope of the embodiments, unless otherwise indicated. Pure stereoisomers (or enriched mixtures) can be prepared using, for example, optically active starting materials or stereoselective reagents well-known in the art. Alternatively, racemic mixtures of such compounds can be separated using, for example, chiral column chromatography, chiral resolving agents and the like.

In certain embodiments, levodopa prodrugs can be prepared by methods well known in the art (see Greene et al., *Protective Groups in Organic Synthesis*, Third Edition, John Wiley & Sons, 1999, and references cited therein; Larock, *Comprehensive Organic Transformations*, John Wiley & Sons, Second Edition, 1999; March, *Advanced Organic Chemistry*, John Wiley & Sons, Fourth Edition, 1992; Smith, *Organic Synthesis*, John Wiley & Sons, 1994; U.S. Pat. No. 4,966,915; U.S. Pat. No. 5,462,933. The disclosures of these references are herein incorporated by reference.

Some of the preparative methods can be found in U.S. Provisional Application No. 60/238,758 and International Publication No. WO 02/28882.

A compound of Formula I can be prepared as illustrated in Scheme 1 below. Reacting Boc-protected levodopa (2) with a halide of Formula (3) in the presence of an appropriate base such as alkali metal bicarbonate or carbonate followed by hydrolysis of the Boc protecting group under acidic conditions affords a compound of Formula I.

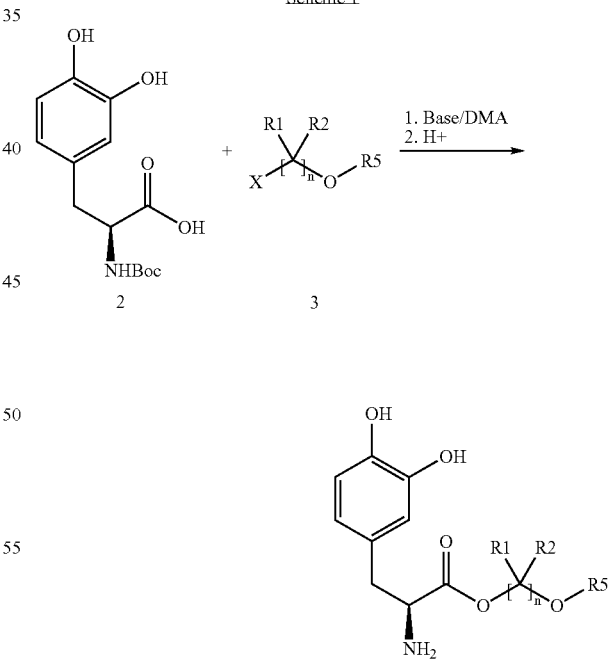

Alternatively, treatment of an appropriate levodopa derivative (4) with an alcohol (5) under standard coupling conditions (Scheme 2) followed by removing the protecting groups provides a compound of Formula I.

Scheme 2

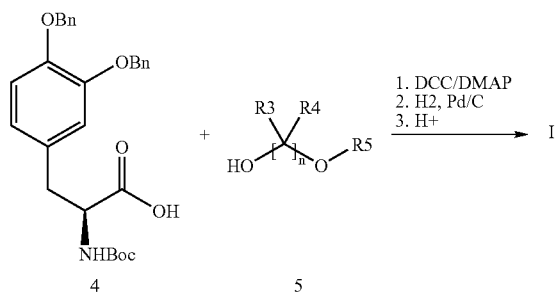

With appropriate manipulation and protection of any chemical functionalities, synthesis of the remaining compounds of Formula (I) can be accomplished by methods analogous to those described above and in the experimental section.

Therapeutic Uses of Certain Compounds

In accordance with certain embodiments, levodopa prodrugs are precursors of dopamine. Thus, the levodopa prodrugs of Formula (I), can be administered to a patient, such as a human, to arrest, ameliorate, reduce the risk of acquiring, reduce the development of or at least one of the clinical symptoms of, or reduce the risk of developing or at least one of the clinical symptoms of, Parkinson's disease. In certain embodiments, levodopa prodrugs of Formula I and compositions comprising at least one levodopa prodrug of Formula I can be coadministration with at least one other therapeutic agent or drug such as a decarboxylase inhibitor which can be effective as a protectant to inhibit or prevent decarboxylation of the levodopa and/or the levodopa prodrugs.

The levodopa prodrugs can be delivered from the same dosage form as the decarboxylase inhibitor, or from a different dosage form. The levodopa prodrugs can be administered at the same time as, prior to, or subsequent to, the administration of a decarboxylase inhibitor. The levodopa prodrugs, together with a decarboxylase inhibitor or decarboxylase inhibitor prodrug or derivative, can be administered to a patient, such as a human, to arrest, ameliorate, reduce the risk of acquiring, reduce the development of or at least one of the clinical symptoms of, or reduce the risk of developing or at least one of the clinical symptoms of, Parkinson's disease.

Certain embodiments of compounds and compositions comprising at least one levodopa prodrug together with at least one decarboxylase inhibitor prodrug can be advantageously used in human medicine. As disclosed herein, in certain embodiments, the compounds and compositions can be useful for the treatment of Parkinson's disease. When used to treat Parkinson's disease, levodopa prodrugs can be administered or applied in combination with at least one decarboxylase inhibitor such as carbidopa and/or a carbidopa prodrug, or benserazide and/or a benserazide prodrug. Additionally, the therapeutic effectiveness of the above combinations can be further enhanced by co-administration of another pharmaceutically active agent such as a catechol oxygen methyl transferase (COMT) inhibitor. Further, in certain embodiments, the levodopa prodrugs, can be administered to a patient, such as a human, together with (i) a decarboxylase inhibitor such as carbidopa and/or a carbidopa prodrug, and (ii) a pharmaceutically active agent such as a catechol oxygen methyl transferase (COMT) inhibitor, to arrest, ameliorate, reduce the risk of acquiring, reduce the development of or at least one of the clinical symptoms of, or reduce the risk of developing or at least one of the clinical symptoms of, Parkinson's disease.

In certain embodiments, the levodopa prodrugs can be administered orally. Certain levodopa prodrugs can also be administered by any other convenient route, such as for example, by infusion, or by absorption through epithelial or mucocutaneous linings (e.g., oral mucosa, rectal and intestinal mucosa).

In certain embodiments, the compounds and/or compositions provide levodopa and levodopa prodrugs upon in vivo administration to a patient. The promoiety or promoieties of the levodopa prodrugs are currently believed to be cleaved either chemically and/or enzymatically. One or more enzymes, such as esterases, present in the stomach, intestinal lumen, intestinal tissue, blood, liver, brain or any other suitable tissue of a mammal can enzymatically cleave the promoiety or promoieties of the compounds and/or compositions. The mechanism of cleavage is not important to the embodiments.

The promoiety or promoieties of certain embodiments of the compounds and/or compositions can be designed to be cleaved after absorption by the gastrointestinal tract, for example in intestinal tissue, blood, liver or other suitable tissue of a mammal. In this situation, levodopa prodrugs can be absorbed into the systemic circulation from the small and large intestines either by active transport, passive diffusion or by both active and passive processes. In certain embodiments, levodopa prodrugs are actively transported across the intestinal endothelium by organic cation transporters expressed throughout the gastrointestinal tract including the small intestine and colon.

Certain compounds and/or compositions comprising at least one levodopa prodrug can be administered as sustained release systems. In certain embodiments, the compounds can be delivered by oral sustained release administration. In some embodiments, the compounds can be administered twice per day, in certain embodiments, once per day, and in certain embodiments at intervals greater than once per day.

Certain levodopa prodrugs can be useful in treating Parkinsonism by administration of one or more of the levodopa prodrugs together with a decarboxylase inhibitor such as carbidopa or a prodrug of carbidopa, in certain embodiments by the oral route, to a mammalian subject in need of the treatment. In a human subject weighing 70 kg, a levodopa prodrug can be administered at a dose having an equivalent weight of levodopa ranging from 10 mg to 10 g per day, and in certain embodiments, having an equivalent weight of levodopa ranging from 100 mg to 3 g per day. The dose can be adjusted by one skilled in the art based on several factors, e.g. the body weight and/or condition of the subject treated, the amount of the decarboxylase inhibitor or prodrug of a decarboxylase inhibitor being administered, the severity of the Parkinson's disease, and the incidence of side effects, the manner of administration and the judgment of the prescribing physician. Dosage ranges can be determined by methods known to those skilled in the art.

The levodopa prodrugs can be assayed in vitro and in vivo, for the desired therapeutic or prophylactic activity prior to use in humans. For example, in vitro assays can be used to determine whether administration of a specific levodopa prodrug is a substrate of a transporter protein, including organic cation transporters such as OCTN1 and OCTN2. Examples of certain assay methods applicable to analyzing the ability of a specfic levodopa prodrug to act as a substrate for a transporter protein are disclosed in Zerangue, et al., U.S. Appl. Pub. No. 2003/0158254. In vitro assays can also be used to determine whether administraton of a specific levodopa prodrug is therapeutically effective. Levodopa prodrugs can also be demonstrated to be effective and safe using animal model systems.

In certain embodiments, a therapeutically effective dose of a levodopa prodrug can provide therapeutic benefit without causing substantial toxicity. Toxicity of levodopa prodrugs can be determined using standard pharmaceutical procedures and can be ascertained by the skilled artisan. The dose ratio between toxic and therapeutic effect is the therapeutic index. Certain levodopa prodrugs can exhibit particularly high therapeutic indices in treating diseases and disorders. The dosage of a levodopa prodrug can be within a range of circulating concentrations that include a therapeutically effective amount of the levodopa prodrug with little or no toxicity.

In addition to the use of the levodopa prodrugs and compositions comprising levodopa prodrugs of the present disclosure for treating Parkinson's disease, in certain embodiments the prodrugs and compositions of the present disclosure can also be useful for treating other dopamine-related diseases. Dopamine-related diseases can be characterized by either insufficient or excessive functional dopaminergic activity in the central nervous system. Examples of other dopamine-related diseases include, but are not limited to, affective disorders such as depression and attention deficit disorder, psychotic disorders such as schizophrenia and manic depression, cognitive impairment disorders, movement disorders such as restless legs syndrome, periodic limb movement disorders, tardive dyskinesia, hypertension, Huntington's disease, and Tourette's syndrome, addictive disorders, congestive heart failure, and excessive daytime sleepiness. For the treatment of these diseases, a levodopa prodrug can be coadministered with an additional active agent. Therapeutically effective doses for treating dopamine-related diseases can be determined by the methods disclosed herein for the treatment of Parkinson's disease and by methods known in the art.

Formulations of Certain Compounds

In some embodiments, levodopa prodrugs can be incorporated into pharmaceutical compositions to be administered orally. Oral administration of such pharmaceutical compositons can result in uptake of the levodopa prodrugs throughout the intestine and entry into the systemic circulation. Such compositions can be prepared in a manner well known in the pharmaceutical art and comprise at least one levodopa prodrug. The present compositions can contain a therapeutically effective amount of at least one levodopa prodrug, in some embodiments, in purified form, together with a decarboxylase inhibitor such as carbidopa, and/or a carbidopa prodrug, and a suitable amount of a pharmaceutically acceptable vehicle, so as to provide an appropriate form for administration to a patient.

Certain embodiments also include compositions that comprise, as the active ingredient, at least one levodopa prodrug, associated with pharmaceutically acceptable excipients, carriers, diluents and/or adjuvants. In forming the compositions, the active ingredient can be mixed with an excipient, diluted by an excipient or enclosed within such a carrier, which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, and syrups containing, for example, up to 90% by weight of the active compound using, for example, soft and hard gelatin capsules.

In preparing a composition, it can be useful to mill the active compound to provide an appropriate particle size prior to combining with other ingredients. For example, if the active compound is substantially insoluble, the active compound can be milled to a particle size of less than 200 mesh. If the active compound is substantially water soluble, the particle size of the active compound can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methylcellulose. The compositions can additionally include lubricating agents such as talc, magnesium stearate, and mineral oil, wetting agents, emulsifying and suspending agents, preserving agents such as methyl- and propylhydroxy-benzoates, sweetening agents, pH adjusting and buffering agents, toxicity adjusting agents, flavoring agents, and the like. The compositions can be formulated so as to provide quick, sustained or delayed release of the active ingredient after administration to the patient by employing procedures known in the art.

A composition can be formulated in unit dosage form, with each dosage comprising the equivalent of from 10 mg to 10 g of levodopa. "Unit dosage form" refers to a physically discrete unit suitable as a unitary dosage for humans and other mammals, each unit containing a predetermined quantity of active material calculated to produce the desired therapeutic effect, in association with a suitable pharmaceutical excipient, diluent, carrier and/or adjuvant.

A levodopa prodrug can be administered in a therapeutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredients can be mixed with a pharmaceutical excipient, diluent, carrier and/or adjuvant to form a solid preformulation composition containing a homogeneous mixture of a levodopa prodrug. When referring to these preformulation compositions as homogeneous, it is meant that the active ingredient is dispersed evenly throughout the composition so that the composition can be readily subdivided into equally effective unit dosage forms such as tablets, pills and capsules. This solid preformulation can then be subdivided into unit dosage forms of the type described herein containing, for example, from 10 mg to 10 g equivalents of levodopa.

Tablets or pills comprising a levodopa prodrug can be coated or otherwise compounded to provide a dosage form affording the advantage of sustained release. For example, a tablet or pill can comprise an inner dosage and an outer dosage component, the latter being in the form of an envelope over and/or enclosing the former. The two components can be separated by an enteric layer. The enteric layer can serve to resist disintegration in the stomach and permit the inner component to pass intact into the duodenum, or to delay release. A variety of materials can be used for such enteric layers or coatings. For example, such materials include a number of polymeric acids and mixtures of polymeric acids with such materials as shellac, cetyl alcohol, and cellulose acetate.

The liquid forms in which the compositions comprising levodopa prodrugs can be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Sustained Release Oral Dosage Forms

Certain levodopa prodrugs can be practiced with a number of different dosage forms, which can be adapted to provide sustained release of the levodopa prodrug upon oral administration.

In certain embodiments, the dosage form can comprise beads that on dissolution or diffusion release the prodrug over an extended period of hours, in some embodiments, over a period of at least 4 hours, in some embodiments, over a period of at least 8 hours, over a period of at least 12 hours, over a period of at least 24 hours, and in other embodiments, over a period of more than 24 hours. The prodrug-releasing beads can have a central composition or core comprising a prodrug and pharmaceutically acceptable vehicles, including an optional lubricant, antioxidant and buffer. Suitable timed-release beads are disclosed in Lu, *Int. J. Pharm.*, 1994, 112, 117-124; Pharmaceutical Sciences by Remington, 14$^{th}$ ed, pp. 1626-1628 (1970); Fincher, *J. Pharm. Sci.*, 1968, 57, 1825-1835; and U.S. Pat. No. 4,083,949). Suitable tablets are disclosed in Pharmaceutical Sciences by Remington, 17$^{th}$ Ed, Ch. 90, pp. 1603-1625 (1985).

In certain embodiments, an oral sustained release pump can be used (see Langer, 1990, *Science*, 249:1527-1533; Sefton, 1987, CRC Crit. Ref. Biomed. Eng., 14:201; Saudek et al., 1989, *N. Engl. J. Med.*, 321:574).

In certain embodiments, polymeric materials can be used for oral sustained release delivery such as described, for example, in "Medical Applications of Controlled Release," Langer and Wise (eds.), CRC Press, Boca Raton, Fla. (1974); "Controlled Drug Bioavailability," Drug Product Design and Performance, Smolen and Ball (eds.), Wiley, New York (1984); Ranger and Peppas, 1983, *J. Macromol. Sci. Rev. Macromol Chem.*, 23:61; Levy et al., 1985, *Science*, 228: 190; During et al., 1989, *Ann. Neurol.*, 25:351; and Howard et al., 1989, *J. Neurosurg.*, 71:105.

In certain embodiments, enteric-coated preparations can be used for oral sustained release administration. In certain embodiments, coating materials include polymers with a pH-dependent solubility (i.e., pH-controlled release), polymers with a slow or pH-dependent rate of swelling, dissolution or erosion (i.e., time-controlled release), polymers that can be degraded by enzymes (i.e., enzyme-controlled release) and polymers that form firm layers that can be destroyed by an increase in pressure (i.e., pressure-controlled release).

In certain embodiments, drug-releasing lipid matrices or prodrug-releasing waxes can be used for oral sustained release administration.

In certain embodiments, a controlled-release system can be placed in proximity to the target of the levodopa prodrug, thus requiring only a fraction of the systemic dose (see Goodson, in "Medical Applications of Controlled Release," supra, vol. 2, pp. 115-138 (1984)). Other controlled-release systems discussed in Langer, 1990, *Science*, 249:1527-1533 can also be used.

In certain embodiments, a dosage form can comprise at least one levodopa prodrug coated on a polymer substrate.

The polymer can be an erodible, or a nonerodible polymer. Representative biodegradable polymers are described, for example, in Rosoff, Controlled Release of Drugs, Chap. 2, pp. 53-95 (1989); and U.S. Pat. Nos. 3,811,444; 3,962,414; 4,066,747; 4,070,347; 4,079,038; and 4,093,709.

In certain embodiments, a dosage form can comprise at least one levodopa prodrug loaded into a polymer that releases the prodrug by diffusion through a polymer, or by flux through pores or by rupture of a polymer matrix as described, for example, in Coleman et al., *Polymers*, 1990, 31, 1187-1231; Roerdink et al., *Drug Carrier Systems*, 1989, 9, 57-100; Leong et al., *Adv. Drug Delivery Rev.*, 1987, 1, 199-233; Roff et al., Handbook of Common Polymers, 1971, CRC Press; and U.S. Pat. No. 3,992,518.

In certain embodiments, osmotic delivery systems can be used for oral sustained release administration (see Verma et al., *Drug Dev. Ind. Pharm.*, 2000, 26:695-708).

Regardless of the specific form or device of sustained release oral dosage form used, a levodopa prodrug can be released from the dosage form, e.g., an orally administered dosage form, over a sufficient period of time to provide prolonged therapeutic concentrations of levodopa in the blood of a patient enabling administration of the dosage form on only a once or twice per day basis. In certain embodiments, the levodopa prodrug can maintain a therapeutic or prophylactic blood concentration of levodopa or levodopa prodrug in the systemic circulation of a patient following oral administration of a levodopa prodrug over a period of at least 4 hours, in certain embodiments, over a period of at least 8 hours, and in certain embodiments, over a period of at least 12 hours.

The compositions can be administered for prophylactic and/or therapeutic treatments. A therapeutic amount is an amount sufficient to remedy a disease state or symptoms, or otherwise prevent, hinder, retard, or reverse the progression of disease or any other undesirable symptoms in any way whatsoever. In prophylactic applications, compositons are administered to a patient susceptible to or otherwise at risk of a particular disease or infection. Hence, a prophylactically effective amount is an amount sufficient to prevent, hinder or retard a disease state or its symptoms. The precise amount of compound contained in a composition can depend on a patient's state of health and weight.

An appropriate dosage of the pharmaceutical compostion can be determined according to any one of several well-established protocols. For example, animal studies, such as studies using mice or rats, can be used to determine an appropriate dose of a pharmaceutical compound. The results from animal studies can be extrapolated to determine doses for use in other species, such as for example, humans.

In certain embodiments, the dosage forms can be administered twice per day, in some embodiments once per day, and in some embodiments, at longer intervals.

Certain embodiments can be further defined by reference to the following examples, which describe in detail preparation of compounds and compositions comprising at least one levodopa prodrug and derivatives thereof and assays for using compounds and compositions comprising at least one levodopa prodrug and derivatives thereof. It will be apparent to those skilled in the art that many modifications, both to materials and methods, can be practiced without departing from the embodiments.

EXAMPLES

The following synthetic and biological examples are offered to illustrate certain embodiments and are not to be construed in any way as limiting the scope. Unless otherwise stated, all temperatures are in degrees Celsius. In the examples below, the following abbreviations have the following meanings. If an abbreviation is not defined, it has its generally accepted meaning.

Å=angstrom
DCM=dichloromethane
DMA=N,N-Dimethylacetamide
DMSO=dimethylsulfoxide
eq=equivalents
EtOAc=ethyl acetate
g=gram
hr=hour
L=liter
LC/MS=liquid chromatography/mass spectroscopy
M=molar
mg=milligram
min=minute
mL=milliliter
mmol=millimoles
Pd—C=palladium on activated carbon
TEA=tetraethylammonium
μL=microliter
μg=microgram Example 1

2-(4-Fluorophenoxy)ethyl (2S)-2-amino-3-(3,4-dihydroxyphenyl)propanoate hydrochloride A suspension of N-Boc-(L)-dopa (20.0, 67.27 mmol), 2-(4-fluorophenoxy)ethyl bromide (0.95 eq) and potassium bicarbonate (1.1 eq) in DMA (100 mL) was stirred at 65° C. overnight. The reacted mixture was diluted with EtOAc (750 mL), washed with water (2×200 mL) and saturated NaHCO$_3$ (2×200 mL), brined, dried over Na$_2$SO$_4$, concentrated under reduced pressure, and purified by column chromatography on silica gel (60 Å, 200-400 Mesh) eluting with 3:7 EtOAc/Hexane to give a clear oil.

The oil was dissolved in a solution of HCl/1,4-dioxane (4.0M, 100 mL), and the mixture was stirred at room temperature for 1 hour before concentrating under reduced pressure to a solid. After dissolving the solid in a minimal amount of acetonitrile (100 mL), the solution was chilled to 4° C., and the resulting white precipitate was collected on a Buchner funnel, washed with diethyl ether (3×50 mL) and dried under high vacuum to afford the title compound as a solid: $^1$H NMR (d$_6$-DMSO): δ 2.92 (m, 2H), 4.14 (m, 2H), 4.21 (t, J=6.4 Hz, 1H), 4.42 (t, J=4.4 Hz, 2H), 6.43 (d, J=7.6 Hz, 1H), 6.59 (s, 1H), 6.60 (d, J=8.0 Hz, 1H), 6.94 (m, 2H), 712 (3, 2H), 8.40 (s, 3H), 8.90 (m, 2H). MS (ESI) m/z 336 (M+H)$^+$ and 334 (M−H)$^−$.

Example 2

2-(4-Chlorophenoxy)ethyl (2S)-2-amino-3-(3,4-dihydroxyphenyl)propanoate hydrochloride The title compound (74 mg, 34% yield) was prepared as a solid following the procedure described in Example 1 but substituting 2-(4-fluorophenoxy)ethyl bromide with 2-(4-chlorophenoxy)ethyl bromide. $^1$H NMR (CD$_3$OD): δ 3.07 (m, 2H), 4.23 (m, 2H), 4.25 (t, J=7.2 Hz, 1H), 4.55 (m, 2H), 6.55 (d, J=8.0 Hz, 1H), 6.68 (s, 1H), 6.70 (d, J=10.0 Hz, 1H), 6.92 (m, 2H), 7.27 (m, 2H). MS (ESI) m/z 352 (M+H)$^+$ and 350 (M−H)$^−$.

Example 3

2-(4-Methylphenoxy)ethyl (2S)-2-amino-3-(3,4-dihydroxyphenyl)propanoate hydrochloride The title compound (77 mg, 23% yield) was prepared as a solid following the procedure described in Example 1 but substituting 2-(4-fluorophenoxy)ethyl bromide with 2-(4-methylphenoxy)ethyl bromide. $^1$H NMR (CD$_3$OD): δ 3.06 (m, 2H), 4.19 (m, 2H), 4.24 (t, J=6.0 Hz, 1H), 4.54 (m, 2H), 6.55 (d, J=8.4 Hz, 1H), 6.68 (s, 1H), 6.70 (d, J=8.4 Hz, 1H), 6.82 (d, J=8.8 Hz, 2H), 7.08 (m, J=8.8 Hz, 2H). MS (ESI) m/z 332 (M+H)$^+$ and 330 (M−H)$^−$.

Example 4

2-(4-Methoxyphenoxy)ethyl (2S)-2-amino-3-(3,4-dihydroxyphenyl)propanoate hydrochloride The title compound (61 mg, 25% yield) was prepared as a solid following the procedure described in Example 1 but substituting 2-(4-fluorophenoxy)ethyl bromide with 2-(4-methoxyphenoxy)ethyl bromide. $^1$H NMR (CD$_3$OD): δ 3.06 (m, 2H), 4.15 (m, 2H), 4.23 (t, J=6.0 Hz, 1H), 4.54 (m, 2H), 6.55 (d, J=8.0 Hz, 1H), 6.68 (s, 1H), 6.70 (d, J=7.6 Hz, 1H), 6.85 (m, 4H). MS (ESI) m/z 348 (M+H)$^+$ and 346 (M−H)$^−$.

Example 5

2-(2-Fluorophenoxy)ethyl (2S)-2-amino-3-(3,4-dihydroxyphenyl)propanoate hydrochloride The title compound (1.83 g, 36% yield) was prepared as a solid following the procedure described in Example 1 but substituting 2-(4-fluorophenoxy)ethyl bromide with 2-(2-fluorophenoxy)ethyl bromide. $^1$H NMR (CD3OD): δ 3.12 (m, 2H), 4.23 (m, 2H), 4.28 (t, J=5.2 Hz, 1H), 4.58 (m, 2H), 6.55 (d, J=8.4 Hz, 1H), 6.67 (s, 1H), 6.70 (d, J=8.0 Hz, 1H), 6.85 (m, 1H), 7.09 (m, 3H). MS (ESI) m/z 336 (M+H)$^+$ and 334 (M−H)$^−$.

Example 6

2-(4-Butylphenoxy)ethyl (2S)-2-amino-3-(3,4-dihydroxyphenyl)propanoate hydrochloride The title compound (300 mg, 40% yield) was prepared as a solid following the procedure described in Example 1 but substituting 2-(4-fluorophenoxy)ethyl bromide with 2-(4-butylphenoxy)ethyl bromide. $^1$H NMR (CD3OD): δ 0.92 (t, J=7.2 Hz, 3H), 1.33 (s, J=7.6 Hz, 2H), 1.55 (q, J=7.6 Hz, 2H), 2.54 (t, J=7.6 Hz, 2H), 3.03 (m, 2H), 4.11 (t, J=6.8 Hz, 1H), 4.17 (m, 2H), 4.51 (m, 2H), 6.54 (d, J=8.4 Hz, 1H), 6.66 (s, 1H), 6.69 (d, J=8.0 Hz, 1H), 6.82 (m, 2H), 7.07 (m, 2H). MS (ESI) m/z 374 (M+H)$^+$ and 372 (M−H)$^−$.

Example 7

2-(3-Fluorophenoxy)ethyl (2S)-2-amino-3-(3,4-dihydroxyphenyl)propanoate hydrochloride The title compound (2.2 g, 42% yield) was prepared as a solid following the procedure descibed in Example 1 but substituting 2-(4-fluorophenoxy)ethyl bromide with 2-(3-fluorophenoxy)ethyl bromide. $^1$H NMR (d$_6$-DMSO): δ 2.88 (m, 2H), 4.16 (m, 3H), 4.40 (t, J=4.0 Hz, 2H), 6.39 (d, J=7.6 Hz, 1H), 6.56 (s, 1H), 6.57 (d, J=8.0 Hz, 1H), 6.75 (m, 3H), 7.28 (q, J=7.2 Hz, 1H), 8.35 (s, 3H), 8.86 (s, 1H), 8.88 (s, 1H). MS (ESI) m/z 336 (M+H)⁺ and 334 (M−H)⁻.

Example 8

2-(4-tert-Butylphenoxy)ethyl (2S)-2-amino-3-(3,4-dihydroxyphenyl)propanoate hydrochloride The title compound (1.7 g, 32% yield) was prepared as a solid following the procedure described in Example 1 but substituting 2-(4-fluorophenoxy)ethyl bromide with 2-(4-t-butylphenoxy)ethyl bromide. ¹H NMR (d₆-DMSO): δ 1.20 (s, 9H), 2.87 (m, 2H), 4.10 (m, 2H), 4.16 (t, J=6.0 Hz, 1H), 4.37 (t, J=4.4 Hz, 2H), 6.40 (d, J=8.0 Hz, 1H), 6.56 (s, 1H), 6.58 (d, J=8.0 Hz, 1H), 6.80 (d, J=8.4 Hz, 2H), 7.24 (d, J=8.4 Hz, 2H), 8.32 (s, 3H), 8.87 (s, 1H), 8.89 (s, 1H). MS (ESI) m/z 374 (M+H)⁺ and 372 (M−H)⁻.

Example 9

2-(4-Isopropylphenoxy)ethyl (2S)-2-amino-3-(3,4-dihydroxyphenyl)propanoate hydrochloride The title compound (1.7 g, 31% yield) was prepared as a solid following the procedure described in Example 1 but substituting 2-(4-fluorophenoxy)ethyl bromide with 2-(4-isopropylphenoxy)ethyl bromide. ¹H NMR (d₆-DMSO): δ 1.11 (d, J=7.2 Hz, 6H), 2.77 (s, J=6.8 Hz, 1H), 2.86(m, 2H), 4.07 (m, 2H), 4.16 (t, J=6.0 Hz, 1H), 4.37 (t, J=4.4 Hz, 2H), 6.39 (d, J=8.0 Hz, 1H), 6.55 (s, 1H), 6.57 (d, J=8.0 Hz, 1H), 6.80 (d, J=8.4 Hz, 2H), 7.10 (d, J=8.4 Hz, 2H), 8.31 (s, 3H), 8.86 (s, 1H), 8.87 (s, 1H). MS (ESI) m/z 360 (M+H)⁺ and 358 (M−H)⁻.

Example 10

2-(4-Ethylphenoxy)ethyl (2S)-2-amino-3-(3,4-dihydroxyphenyl)propanoate hydrochloride The title compound (2.1 g, 42% yield) was prepared as a solid following the procedure described in Example 1 but substituting 2-(4-fluorophenoxy)ethyl bromide with 2-(4-ethylphenoxy)ethyl bromide. ¹H NMR (d₆-DMSO): δ 1.09 (t, J=7.6 Hz, 3H), 2.49 (q, J=7.2 Hz, 2H), 2.87 (m, 2H), 4.08 (m, 2H), 4.18 (t, J=6.0 Hz, 1H), 4.39 (t, J=4.4 Hz, 2H), 6.39 (d, J=8.0 Hz, 1H), 6.55 (s, 1H), 6.57 (d, J=8.0 Hz, 1H), 6.79 (d, J=8.8 Hz, 2H), 7.07 (d, J=8.8 Hz, 2H), 8.26 (s, 3H), 8.85 (s, 1H), 8.88 (s, 1H). MS (ESI) m/z 346 (M+H)⁺ and 344 (M−H)⁻.

Example 11

2-(2,4-Dimethylphenoxy)ethyl (2S)-2-amino-3-(3,4-dihydroxyphenyl)propanoate hydrochloride The title compound (1.1 g, 23% yield) was prepared as a solid following the procedure described in Example 1 but substituting 2-(4-fluorophenoxy)ethyl bromide with 2-(2,4-dimethylphenoxy)ethyl bromide. ¹H NMR (d₆-DMSO): δ 2.07 (s, 3H), 2.15 (s, 3H), 2.88 (m, 2H), 4.08 (t, J=6.4 Hz, 1H), 4.17 (t, J=4.8 Hz, 2H), 4.40 (m, 2H), 6.36 (d, J=8.4 Hz, 1H), 6.54 (d, J=8.0 Hz, 1H), 6.56 (s, 1H), 6.75 (d, J=8.8 Hz, 1H), 6.89 (m, 2H), 8.34 (s, 3H), 8.86 (s, 1H), 8.88 (s, 1H). MS (ESI) m/z 346 (M+H)⁺ and 344 (M−H)⁻.

Example 12

2-(3,4-Dimethylphenoxy)ethyl (2S)-2-amino-3-(3,4-dihydroxyphenyl)propanoate hydrochloride The title compound (2.4 g, 36% yield) was prepared as a solid following the procedure described in Example 1 but substituting 2-(4-fluorophenoxy)ethyl bromide with 2-(3,4-dimethylphenoxy)ethyl bromide. ¹H NMR (d₆-DMSO): δ 2.09 (s, 3H), 2.14 (s, 3H), 2.86(m, 2H), 4.06 (m, 2H), 4.17 (t, J=6.0 Hz, 1H), 4.37 (t, J=4.4 Hz, 2H), 6.39 (d, J=8.0 Hz, 1H), 6.55 (s, 1H), 6.57 (d, J=8.0 Hz, 1H), 6.60 (d, J=8.4 Hz, 2H), 6.69 (s, 1H), 6.98 (d, J=8.4 Hz, 1H), 8.32 (s, 3H), 8.86 (s, 1H), 8.88 (s, 1H). MS (ESI) m/z 346 (M+H)⁺ and 344 (M−H)⁻.

Example 13

2-(4-Fluorophenoxy)ethyl (2S)-2-amino-3-(3,4-diethoxycarbonyloxyphenyl)propanoate hydrochloride The title compound was (2.24 g, 49% yield) prepared as a solid following the procedure described in Example 1, however, before final acid deprotection of the Boc group, the compound's catechol moiety was first reacted with ethyl chloroformate (2.5 eq.) with TEA (4.0 eq) as a base and DCM (35 mL) as the reacting solvent at room temperature for 2 hrs. This reaction mixture was concentrated to a small volume, diluted with EtOAc (250 mL), washed with water (2×100 mL) and saturated NaHCO₃ (3×100 mL), brined, dried over Na₂SO₄, and concentrated to an oil. ¹H NMR (d₆-DMSO): δ 1.21 (q, J=6.8 Hz, 6H), 3.09 (m, 2H), 4.06 (m, 2H), 4.18(t, J=7.2 Hz, 4H), 4.36 (m, 3H), 6.87 (m, 2H), 7.05 (m, 2H), 7.13 (d, J=8.0 Hz, 1H), 7.25 (m, 2H), 8.45 (s, 3H). MS (ESI) m/z 480 (M+H)⁺.

Example 14

3-Phenoxypropyl (2S)-2-amino-3-(3,4-dihydroxyphenyl)propanoate hydrochloride

The title compound (1.0 g, 30% yield) was prepared as a solid following the procedure described in Example 1 but substituting 2-(4-fluorophenoxy)ethyl bromide with 3-phenoxypropyl bromide. ¹H NMR (d₆-DMSO): δ 1.93 (m, 2H), 2.85 (m, 2H), 3.87(m, 2H), 4.15 (m, 3H), 6.36 (d, J=8.0 Hz, 1H), 6.52 (s, 1H), 6.57 (d, J=8.0 Hz, 1H), 6.84 (m, 3H), 7.20 (d, J=8.0 Hz, 2H), 8.36 (s, 3H), 8.87 (s, 1H), 8.88 (s, 1H). MS (ESI) m/z 332 (M+H)⁺ and 330 (M−H)⁻.

Example 15

3-(4-Fluorophenoxy)propyl (2S)-2-amino-3-(3,4-dihydroxyphenyl)propanoate hydrochloride The title compound (0.65 g, 33% yield) was prepared as a solid following the procedure described in Example 1 but substituting 2-(4-fluorophenoxy)ethyl bromide with 3-(4-fluorophenoxy)propyl bromide. ¹H NMR (d₆-DMSO): δ 1.90 (m, 2H), 2.90 (m, 2H), 3.80 (m, 2H), 4.08 (m, 1H), 4.17 (m, 2H), 6.36 (d, J=8.0 Hz, 1H), 6.54 (s, 1H), 6.59 (d, J=8.0 Hz, 1H), 6.84 (m, 2H), 7.05 (m, 2H), 8.35 (s, 3H), 8.90 (s, 2H). MS (ESI) m/z 350 (M+H)⁺ and 348 (M−H)⁻.

Example 16

(2R)-2-(4-Fluorophenoxy)isopropyl (2S)-2-amino-3-(3,4-dihydroxyphenyl)propanoate hydrochloride To a solution of N-Cbz-L-DOPA(OBn)$_2$COOH (0.51 g, 1 mmol) and (2R)-1-(4-fluorophenoxy)propan-2-ol (0.2 g, 1.2 mmol) in 20 mL of anhydrous dichloromethane, a solution of 1,3-dicyclohexylcarbodiimide (0.31 g, 1.2 mmol) in dichloromethane was slowly added, followed by addition of a catalytic amount of 4-(dimethylamino)pyridine. The resulting mixture was stirred at room temperature for 16 hrs. After filtration, the filtrate was washed with 5% NaHCO$_3$, brine and dried over Na$_2$SO$_4$. After removing the solvent, chromatography (silica gel, 10% ethyl acetate in hexane) of the residue gave 0.41 g (62%) of a white solid. The white solid and 10% Pd—C (30 mg) was mixed in 10 mL of 20% methanol/tetrahydrafuran. The resulting mixture was stirred under hydrogen at room temperature for 2 hrs. After filtration and washing with methanol, the filtrate was concentrated and purified by using HPLC (0.05% formic acid/water/acetonitrile) followed by lyophilization in the presence of aqueous hydrogen chloride to afford 0.12 g (55%) of the title compound. $^1$H NMR (400 MHz, CD$_3$OD): δ 1.34 (d, J=6.4 Hz, 3H), 3.04 (dd, J=6.8, 14.4 Hz, 1H), 3.09 (dd, J=6.8, 14.4 Hz, 1H), 4.04 (d, J=5.2 Hz, 2H), 4.19 (t, J=6.8 Hz, 1H), 5.31 (m, 1H), 6.57 (dd, J=2, 8 Hz, 1H), 6.68 (d, J=2 Hz, 1H), 6.73 (d, J=8 Hz, 1H), 6.96 (dd, J=5.6, 8.8 Hz, 2H), 7.00 (t, J=8.8 Hz, 2H). MS (ESI) m/z 350.54 (M+H)$^+$ and 348.31 (M−H)$^−$.

Example 17

(2S)-2-(4-Fluorophenoxy)isopropyl (2S)-2-amino-3-(3,4-dihydroxyphenyl)propanoate hydrochloride Following the procedure described in Example 16, and substituting (2R)-1-(4-fluorophenoxy)propan-2-ol with (2S)-1-(4-fluorophenoxy)propan-2-ol, provided the title compound (49% over 2 steps) as a white solid. $^1$H NMR (400 MHz, CD$_3$OD): δ 1.39 (d, J=6.4 Hz, 3H), 3.02 (dd, J=7.2, 14.4 Hz, 1H), 3.08 (dd, J=6.4, 14.4 Hz, 1H), 3.98 (d, J=5.2 Hz, 2H), 4.21 (t, J=6.4 Hz, 1H), 5.33 (m, 1H), 6.56 (dd, J=2, 8 Hz, 1H), 6.67 (d, J=8 Hz, 1H), 6.70 (d, J=2 Hz, 1H), 6.95 (dd, J=4.8, 8.8 Hz, 2H), 7.00 (t, J=8.8 Hz, 2H). MS (ESI) m/z 350.29 (M+H)$^+$ and 348.26 (M−H)$^−$.

Example 18

Uptake of Levodopa Prodrugs Following Administration of Levodopa Prodrugs and Carbidopa in Rats Sustained release oral dosage forms, which release drug slowly over periods of 6 to 24 hours, generally release a significant proportion of the dose within the colon. Thus, drugs suitable for use in such dosage forms can exhibit good colonic absorption. This experiment was conducted to assess the uptake and resultant blood levels of levodopa, following intracolonic administration of levodopa prodrugs with coadministration of carbidopa (intracolonically, intraperitoneally or orally), and thereby determine the suitability of levodopa prodrugs for use in an oral sustained release dosage form. Bioavailability of levodopa following coadminstration of levodopa prodrugs and carbidopa was calculated relative to oral coadministration of levodopa and carbidopa.

Step A: Administration Protocol

Rats were obtained commercially and were pre-cannulated in the both the ascending colon and the jugular vein. Animals were conscious at the time of the experiment. All animals were fasted overnight and until 4 hours post-dosing of levodopa produg. Carbidopa was administered as a solution in water or citrate buffer either orally, or intraperitoneally or intracolonically at a dose equivalent to 25 mg of carbidopa per kg. Either at the same time or 1 hour after carbidopa dosing, levodopa HCl salt or levodopa prodrug HCl salt was administered as a solution (in water) directly into the colon via the cannula at a dose equivalent to 75 mg of levodopa per kg. Blood samples (0.3 mL) were obtained from the jugular cannula at intervals over 8 hours and were quenched immediately by addition of sodium metabisulfite to prevent oxidation of levodopa. Blood was then further quenched with methanol/perchloric acid to prevent hydrolysis of the levodopa prodrug. Blood samples were analyzed as described below.

Step B: Sample Preparation for Colonically Absorbed Drug

1. In blank 1.5 mL tubes, 300 μL of methanol/perchloric acid was added.
2. Rat blood (300 μL) was collected at different times into EDTA tubes containing 75 μL of sodium metabisulfite, and vortexed to mix. A fixed volume of blood (100 μL) was immediately added into the Eppendorf tube and vortexed to mix.
3. Ten microliters of an levodopa standard stock solution (0.04, 0.2, 1, 5, 25, 100 μg/mL) and 10 μL of the 10% sodium metabisulfate was added to 80 μL of blank rat blood to make up a final calibration standard (0.004, 0.02, 0.1, 0.5, 2.5, 10 μg/mL). Then 300 μL of 50/50 methanol/perchloric acid was added into each tube followed by 20 μL of p-chlorophenylalanine.
4. Samples were vortexed and centrifuged at 14,000 rpm for 10 mm.
5. Supernatant was analyzed by LC/MS/MS.

Step C: LC/MS/MS Analysis

An API 4000 LC/MS/MS spectrometer equipped with Agilent 1100 binary pumps and a CTC HTS-PAL autosampler were used in the analysis. A Zorbax XDB C8 4.6×150 mm column was used during the analysis. The mobile phase was 0.1% formic acid (A) and acetonitrile with 0.1% formic acid (B). The gradient condition was: 5% B for 0.5 min, then to 98% B in 3 min, then maintained at 98% B for 2.5 min. The mobile phase was returned to 2% B for 2 min. A TurboIonSpray source was used on the API 4000. The analysis was done in positive ion mode and the MRM transition for each analyte was optimized using standard solution. 5 μL of the samples were injected. Non-compartmental analysis was performed using WinNonlin (v.3.1 Professional Version, Pharsight Corporation, Mountain View, Calif.) on individual animal profiles. Summary statistics on major parameter estimates was performed for $C_{max}$ (peak observed concentration following dosing), $T_{max}$ (time to maximum concentration is the time at which the peak concentration was observed), $AUC_{(0-t)}$ (area under the serum concentration-time curve from time zero to last collection time, estimated using the log-linear trapezoidal method), $AUC_{(0-\infty)}$, (area under the serum concentration time curve from time zero to infinity, estimated using the log-linear trapezoidal method to the last collection time with extrapolation to infinity), and $t_{1/2,z}$ (terminal half-life). Maximum concentrations of levodopa in the blood ($C_{max}$ values) and the area under blood concentration versus time curve (AUC) values after intracolonic dosing of levodopa prodrugs with carbidopa were significantly higher (>2-fold) than those achieved for colonic administration of levodopa with carbidopa.

Intracolonic coadministration of levodopa and carbidopa results in very low relative bioavailability of levodopa (i.e., only 3% of orally coadministered levodopa and carbidopa). By comparison, coadministration of the levodopa prodrugs listed below with carbidopa exhibited improved relative bioavailability of levodopa by at least 2-fold. The range of improved relative bioavailability of levodopa was between 2 and 20 fold. These data demonstrate that certain levodopa prodrugs can be formulated as compositions suitable for effective sustained oral release and uptake of levodopa from the colon.

Levodopa prodrugs which, when administered, produced a relative bioavailability of levodopa at least 2-fold greater than the bioavailability of levodopa produced following the administration of levodopa include:

2-(4-Fluorophenoxy)ethyl (2S)-2-amino-3-(3,4-dihydroxyphenyl)propanoate hydrochloride;
2-(2,4-Dimethylphenoxy)ethyl (2S)-2-amino-3-(3,4-dihydroxyphenyl)propanoate hydrochloride;
2-(3,4-Dimethylphenoxy)ethyl (2S)-2-amino-3-(3,4-dihydroxyphenyl)propanoate hydrochloride;
3-(4-Fluorophenoxy)propyl (2S)-2-amino-3-(3,4-dihydroxyphenyl)propanoate hydrochloride; and
3-Phenoxypropyl (2S)-2-amino-3-(3,4-dihydroxyphenyl)propanoate hydrochloride.

The invention claimed is:
1. A compound of Formula (I):

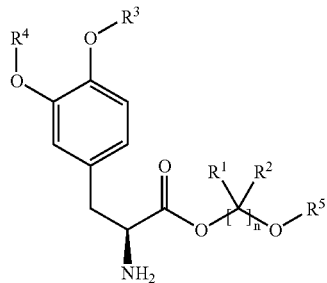

(I)

a stereoisomer thereof, an enantiomer thereof, a pharmaceutically acceptable salt thereof, a hydrate thereof, or a solvate of any of the foregoing, wherein
n is an integer from 1 to 6;
each $R^1$ and $R^2$ is independently selected from hydrogen, alkenyl, alkynyl, substituted alkyl, aryl, substituted aryl, arylalkyl, substituted arylalkyl, cycloalkyl, substituted cycloalkyl, cycloheteroalkyl, substituted cycloheteroalkyl, halo, heteroalkyl, substituted heteroalkyl, heteroaryl, substituted heteroaryl, heteroarylalkyl, and substituted heteroarylalkyl, or optionally, when n is 1, then $R^1$ and $R^2$ together with the carbon atom to which $R^1$ and $R^2$ are attached form a cycloalkyl, substituted cycloalkyl, cycloheteroalkyl or substituted cycloheteroalkyl ring;
$R^3$ and $R^4$ are independently selected from hydrogen, $-C(O)OR^7$, $-C(O)R^7$, and $-(CR^8R^9)OC(O)R^{10}$;

$R^5$ is selected from alkyl, substituted alkyl, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl;
$R^7$ is selected from alkyl, substituted alkyl, cycloalkyl, substituted cycloalkyl, cycloheteroalkyl, substituted cycloheteroalkyl, aryl, substituted aryl, arylalkyl, substituted arylalkyl, heteroaryl, substituted heteroaryl, heteroarylalkyl, and substituted heteroarylalkyl;
$R^8$ and $R^9$ are independently selected from hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, and substituted heteroarylalkyl or optionally, $R^8$ and $R^9$ together with the carbon atom to which $R^8$ and $R^9$ are attached form a cycloalkyl, substituted cycloalkyl, cycloheteroalkyl or substituted cycloheteroalkyl ring; and
$R^{10}$ is selected from hydrogen, alkyl, substituted alkyl, aryl, substituted aryl, arylalkyl, substituted arylalkyl, cycloalkyl, substituted cycloalkyl, heteroalkyl, substituted heteroalkyl, cycloheteroalkyl, substituted cycloheteroalkyl, heteroaryl, substituted heteroaryl, heteroarylalkyl, and substituted heteroarylalkyl;
wherein each substituent group is independently selected from halo, $-CN$, $-NO_2$, $-OH$, $C_{1-6}$ alkyl, and $C_{1-6}$ alkoxy;
with the provisos that
when n is 2, and $R^1$, $R^2$, $R^3$ and $R^4$ are hydrogen, then $R^5$ is not methyl or phenyl;
when n is 3, and $R^1$, $R^2$, $R^3$ and $R^4$ are hydrogen, then $R^5$ is not methyl; and
when n is an integer from 1 to 6, and $R^1$, $R^2$, $R^3$ and $R^4$ are hydrogen, then $R^5$ is not benzyl.

2. A compound according to claim 1, wherein $R^5$ is selected from aryl, substituted aryl, heteroaryl, and substituted heteroaryl.

3. A compound according to claim 1, wherein $R^5$ is selected from $C_{5-8}$ aryl, and substituted $C_{5-8}$ aryl substituted with one or more substituents selected from halo, $-CN$, $-NO_2$, $-OH$, $C_{1-6}$ alkyl, and $C_{1-6}$ alkoxy.

4. A compound according to claim 1, wherein $R^5$ is selected from phenyl and pyridyl, which are optionally substituted with halo, $-CN$, $-OH$, $C_{1-4}$ alkyl, and $C_{1-4}$ alkoxy.

5. A compound according to claim 1, wherein n is 1, and $R^1$ and $R^2$ together with the carbon atoms to which $R^1$ and $R^2$ are attached form a cycloalkanyl, substituted cycloalkanyl, cycloheteroalkanyl or substituted cycloheteroalkanyl ring.

6. A compound according to claim 1, wherein n is 1 and $R^1$ and $R^2$ together with the carbon atoms to which $R^1$ and $R^2$ are attached form a cyclopropyl, cyclobutyl, cyclopentyl or cyclohexyl ring.

7. A compound according to claim 1, wherein each $R^1$ and $R^2$ is hydrogen.

8. A compound according to claim 1, wherein $R^3$ and $R^4$ are independently selected from hydrogen, $-C(O)OR^7$, and $-C(O)R^7$.

9. A compound according to claim 8, wherein $R^7$ is selected from alkanyl, substituted alkanyl, cycloalkanyl, substituted cycloalkanyl, arylalkanyl, substituted arylalkanyl, heteroarylalkanyl, and substituted heteroarylalkanyl.

10. A compound according to claim 8, wherein $R^7$ is selected from methyl, ethyl, propyl, isopropyl, butyl, isobutyl, sec-butyl, tert-butyl, cyclopropyl, cyclobutyl, cyclopentyl, cyclohexyl, and benzyl, where the aryl ring of the benzyl group is optionally substituted with one or more substituents selected from halo, —CN, —NO$_2$, —OH, $C_{1-6}$ alkyl, and $C_{1-6}$ alkoxy.

11. A compound according to claim 8, wherein $R^7$ is selected from aryl, substituted aryl, heteroaryl, and substituted heteroaryl.

12. A compound according to claim 8, wherein $R^7$ is selected from $C_{5-8}$ aryl, $C_{5-8}$ substituted aryl, heteroaryl, substituted heteroaryl, $C_{6-10}$ arylalkyl, and substituted $C_{6-10}$ arylalkyl.

13. A compound according to claim 8, wherein $R^7$ is selected from phenyl, pyridyl, furyl, and thienyl, the aromatic rings of which are optionally substituted with one or more substituents selected from halo, —CN, —NO$_2$, —OH, $C_{1-6}$ alkyl, and $C_{1-6}$ alkoxy.

14. A compound according to claim 1, wherein $R^3$ and $R^4$ are independently selected from hydrogen, and —(CR$^8$R$^9$)OC(O)R$^{10}$.

15. A compound according to claim 14, wherein $R^8$ and $R^9$ are independently selected from hydrogen, $C_{1-16}$ alkyl, substituted $C_{1-16}$ alkyl, $C_{5-8}$ aryl, substituted $C_{5-8}$ aryl, $C_{6-10}$ arylalkyl, and substituted $C_{6-10}$ arylalkyl.

16. A compound according to claim 14, wherein $R^8$ and $R^9$ are independently selected from hydrogen, methyl, ethyl, propyl, isopropyl, butyl, and isobutyl.

17. A compound according to claim 14, wherein $R^{10}$ is selected from hydrogen, $C_{1-10}$ alkyl, substituted $C_{1-10}$ alkyl, $C_{5-8}$ aryl, substituted $C_{5-8}$ aryl, $C_{1-15}$ alkoxy, and substituted $C_{1-5}$ alkoxy.

18. A compound according to claim 14, wherein $R^{10}$ is selected from methyl, ethyl, propyl, isopropyl, butyl, isobutyl, sec-butyl, tert-butyl, cyclopropyl, cyclobutyl, cyclopentyl, cyclohexyl, benzyl, and phenyl, where the aryl ring of the benzyl group is optionally substituted with one or more substituents selected from halo, —CN, —NO$_2$, —OH, $C_{1-6}$ alkyl, and $C_{1-6}$ alkoxy.

19. A compound according to claim 1, wherein $R^5$ is selected from alkanyl, substituted alkanyl, alkenyl, substituted alkenyl, arylalkanyl, substituted arylalkanyl, arylalkenyl, substituted arylalkenyl, cycloalkanyl, substituted cycloalkanyl, cycloheteroalkanyl, substituted cycloheteroalkanyl, heteroarylalkanyl, and substituted heteroarylalkanyl.

20. A compound according to claim 1, wherein $R^5$ is selected from methyl, ethyl, propyl, isopropyl, butyl, isobutyl, sec-butyl, tert-butyl, pentyl, hexyl, cyclopropyl, cyclobutyl, cyclopentyl, cyclohexyl, benzyl, phenethyl, and styryl, where the aryl ring of the benzyl or styryl group is optionally substituted with one or more substituents are selected from halo, —CN, —NO$_2$, —OH, $C_{1-6}$ alkyl, and $C_{1-6}$ alkoxy.

21. A compound according to claim 1 selected from:
2-(4-Fluorophenoxy)ethyl (2S)-2-amino-3-(3,4-dihydroxyphenyl)propanoate;
2-(4-Chlorophenoxy)ethyl (2S)-2-amino-3-(3,4-dihydroxyphenyl)propanoate;
2-(4-Methylphenoxy)ethyl (2S)-2-amino-3-(3,4-dihydroxyphenyl)propanoate;
2-(4-Methoxyphenoxy)ethyl (2S)-2-amino-3-(3,4-dihydroxyphenyl)propanoate;
2-(2-Fluorophenoxy)ethyl (2S)-2-amino-3-(3,4-dihydroxyphenyl)propanoate;
2-(4-Butylphenoxy)ethyl (2S)-2-amino-3-(3,4-dihydroxyphenyl)propanoate;
2-(3-Fluorophenoxy)ethyl (2S)-2-amino-3-(3,4-dihydroxyphenyl)propanoate;
2-(4-tert-Butylphenoxy)ethyl (2S)-2-amino-3-(3,4-dihydroxyphenyl)propanoate;
2-(4-Isopropylphenoxy)ethyl (2S)-2-amino-3-(3,4-dihydroxyphenyl)propanoate;
2-(4-Ethylphenoxy)ethyl (2S)-2-amino-3-(3,4-dihydroxyphenyl)propanoate;
2-(2,4-Dimethylphenoxy)ethyl (2S)-2-amino-3-(3,4-dihydroxyphenyl)propanoate;
2-(3,4-Dimethylphenoxy)ethyl (2S)-2-amino-3-(3,4-dihydroxyphenyl)propanoate;
2-(4-Fluorophenoxy)ethyl (2S)-2-amino-3-(3,4-diethoxycarbonyloxyphenyl)propanoate;
3-Phenoxypropyl (2S)-2-amino-3-(3,4-dihydroxyphenyl)propanoate;
3-(4-Fluorophenoxy)propyl (2S)-2-amino-3-(3,4-dihydroxyphenyl)propanoate;
(2R)-2-(4-Fluorophenoxy)isopropyl (2S)-2-amino-3-(3,4-dihydroxyphenyl)propanoate;
(2S)-2-(4-Fluorophenoxy)isopropyl (2S)-2-amino-3-(3,4-dihydroxyphenyl)propanoate; and
pharmaceutically acceptable salts thereof.

22. A compound according to claim 1 selected from:
2-(4-Fluorophenoxy)ethyl (2S)-2-amino-3-(3,4-dihydroxyphenyl)propanoate;
2-(2,4-Dimethylphenoxy)ethyl (2S)-2-amino-3-(3,4-dihydroxyphenyl)propanoate;
2-(3,4-Dimethylphenoxy)ethyl (2S)-2-amino-3-(3,4-dihydroxyphenyl)propanoate;
3-(4-Fluorophenoxy)propyl (2S)-2-amino-3-(3,4-dihydroxyphenyl)propanoate;
3-Phenoxypropyl (2S)-2-amino-3-(3,4-dihydroxyphenyl)propanoate; and
pharmaceutically acceptable salts thereof.

23. The compound of claim 21 or 22, wherein the pharmaceutically acceptable salt is the hydrochloride salt.

24. A pharmaceutical composition comprising at least one pharmaceutically acceptable excipient, and a therapeutically effective amount of at least one compound of Formula (I) according to claim 1.

25. A pharmaceutical composition according to claim 24, further comprising at least one decarboxylase inhibitor.

26. A pharmaceutical composition according to claim 25, wherein the at least one decarboxylase inhibitor is selected from carbidopa, a carbidopa prodrug, benserazide, and a benserazide prodrug.

27. A pharmaceutical composition according to claim 24, further comprising at least one catechol O-methyltransferase inhibitor.

28. A pharmaceutical composition according to claim 27, wherein the at least one catechol O-methyltransferase inhibitor is selected from entacapone, and tolcapone.

29. A pharmaceutical composition according to claim 24, wherein the pharmaceutical composition is formulated for oral administration.

30. A pharmaceutical composition according to claim 24, wherein the pharmaceutical composition is a sustained release formulation.

31. A pharmaceutical composition according to claim 24, wherein the at least one compound of Formula (I) is present in an amount effective for the treatment in a patient of Parkinson's disease.

32. A pharmaceutical composition according to claim 24, wherein the at least one compound of Formula (I) is present in an amount effective for the treatment in a patient of a disease selected from depression, attention deficit disorder; schizophrenia, manic depression, cognitive impairment disorders, restless legs syndrome, periodic limb movement disorders, Huntington's disease, Tourette's syndrome, congestive heart failure.

33. A compound according to claim 1, which when administered in the colon of a patient is taken up at a rate to achieve a bioavailability of levodopa at least 2-fold greater than the bioavailability of levodopa achieved when levodopa is administered in the colon of the patient.

34. A compound according to claim 1, wherein each $R^1$ and $R^2$ is independently selected from hydrogen, substituted alkanyl, arylalkanyl, substituted arylalkanyl, cycloalkanyl, substituted cycloalkanyl, cycloheteroalkanyl, substituted cycloheteroalkanyl, halo, heteroalkanyl, substituted heteroalkanyl, heteroarylalkanyl, and substituted heteroarylalkanyl.

35. A compound according to claim 1, wherein each $R^1$ and $R^2$ independently selected from hydrogen, cyclopropyl, cyclobutyl, cyclopentyl, cylohexyl, and benzyl.

36. A compound according to claim 1, wherein each $R^1$ and $R^2$ is independently selected from hydrogen, substituted alkanyl, arylalkanyl, aryl, substituted aryl, heteroaryl, and substituted heteroaryl.

37. A compound according to claim 1, wherein each $R^1$ and $R^2$ is independently selected from hydrogen and phenyl, which is optionally substituted with one or more substituents selected from halo, —CN, —NO$_2$, —OH, $C_{1-6}$ alkyl, and $C_{1-6}$ alkoxy.

38. A compound according to claim 1, wherein each $R^1$ and $R^2$ is independently selected from hydrogen and substituted $C_{1-4}$ alkyl.

* * * * *

UNITED STATES PATENT AND TRADEMARK OFFICE
CERTIFICATE OF CORRECTION

PATENT NO. : 7,323,585 B2  Page 1 of 1
APPLICATION NO. : 11/145280
DATED : January 29, 2008
INVENTOR(S) : Jia-Ning Xiang et al.

It is certified that error appears in the above-identified patent and that said Letters Patent is hereby corrected as shown below:

In claim 17, column 31, line 33, "$C_{1-5}$ alkoxy." should read --$C_{1-15}$ alkoxy.--.

In claim 20, column 31, line 52, delete "are".

In claim 32, column 33, line 2, "disorder;" should read --disorder,--.

In claim 32, column 33, lines 5-6, "syndrome, congestive" should read --syndrome, and congestive--.

In claim 35, column 34, line 2, "$R^2$ independently" should read --$R^2$ is independently--.

Signed and Sealed this

Twenty-second Day of June, 2010

David J. Kappos
*Director of the United States Patent and Trademark Office*